(12) United States Patent
Barolat

(10) Patent No.: US 8,942,821 B2
(45) Date of Patent: Jan. 27, 2015

(54) ELECTRODE PADDLE FOR NEUROSTIMULATION

(71) Applicant: Giancarlo Barolat, Golden, CO (US)

(72) Inventor: Giancarlo Barolat, Golden, CO (US)

( * ) Notice: Subject to any disclaimer, the term of this patent is extended or adjusted under 35 U.S.C. 154(b) by 0 days.

(21) Appl. No.: 14/048,962

(22) Filed: Oct. 8, 2013

(65) Prior Publication Data
US 2014/0039580 A1 Feb. 6, 2014

Related U.S. Application Data

(63) Continuation of application No. 11/627,337, filed on Jan. 25, 2007, now Pat. No. 8,554,337.

(51) Int. Cl.
*A61N 1/06* (2006.01)
*A61N 1/05* (2006.01)
*A61N 1/36* (2006.01)

(52) U.S. Cl.
CPC .............. *A61N 1/05* (2013.01); *A61N 1/0553* (2013.01); *A61N 1/3605* (2013.01)
USPC ....................................................... 607/116

(58) Field of Classification Search
USPC ............................................... 607/2, 46, 116
See application file for complete search history.

(56) References Cited

U.S. PATENT DOCUMENTS

| 5,417,719 | A  | * | 5/1995 | Hull et al. ................ 607/46 |
| 7,006,859 | B1 | * | 2/2006 | Osorio et al. ............. 600/378 |
| 7,107,097 | B2 | * | 9/2006 | Stern et al. ................ 607/2 |

* cited by examiner

*Primary Examiner* — Rex R Holmes
(74) *Attorney, Agent, or Firm* — Haynes and Boone, LLP

(57) ABSTRACT

An implantable electrode paddle for use in a neurostimulation system may include a dorsally-projecting lead that allows all of the edges of the electrode paddle to be situated near a vertebral body for stimulation of neural structures. Embodiments may include one or more flanges for cooperating with a vertebral body and thereby stabilizing the electrode paddle. Embodiments of the present invention may also include features to allow an electrode paddle to be divided during surgery. Embodiments of the present invention may also include an electrode paddle having a plurality of paddle sections, wherein at least one of the paddle sections comprises a plurality of asymmetrically configured contacts. Embodiments of the invention include a method of assembling a neurostimulation system and a method of implanting an implantable system in a body, wherein the implantable system includes an electrode paddle that may be divided into a plurality of paddle sections.

14 Claims, 42 Drawing Sheets

Conventional electrode placement at C1-2
Electrode placed in a caudal direction between the occipital bone and C1

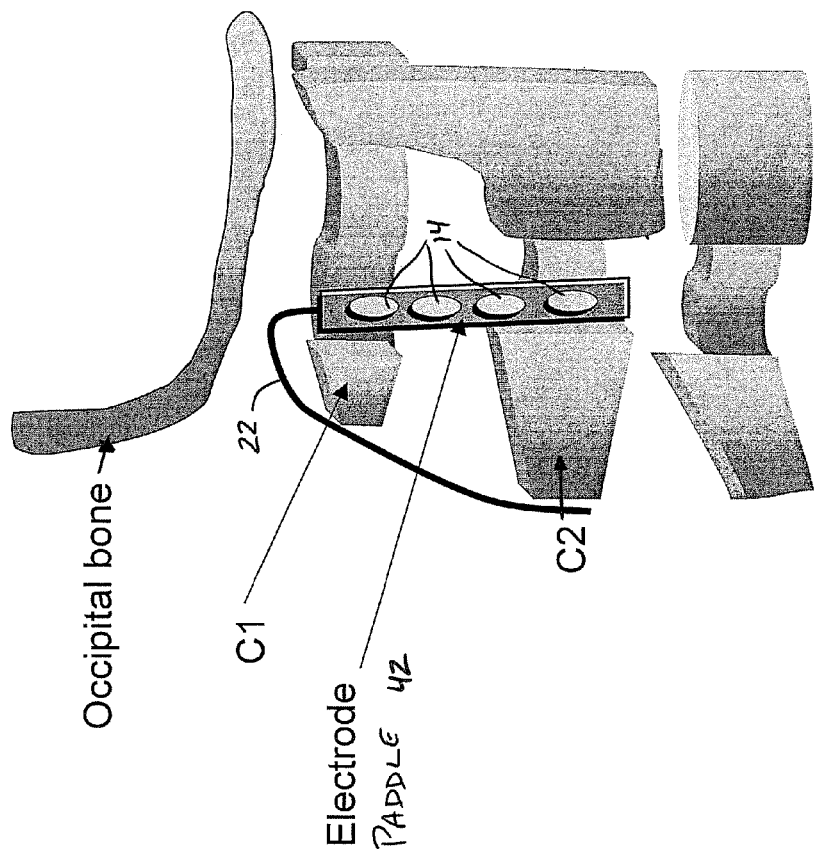

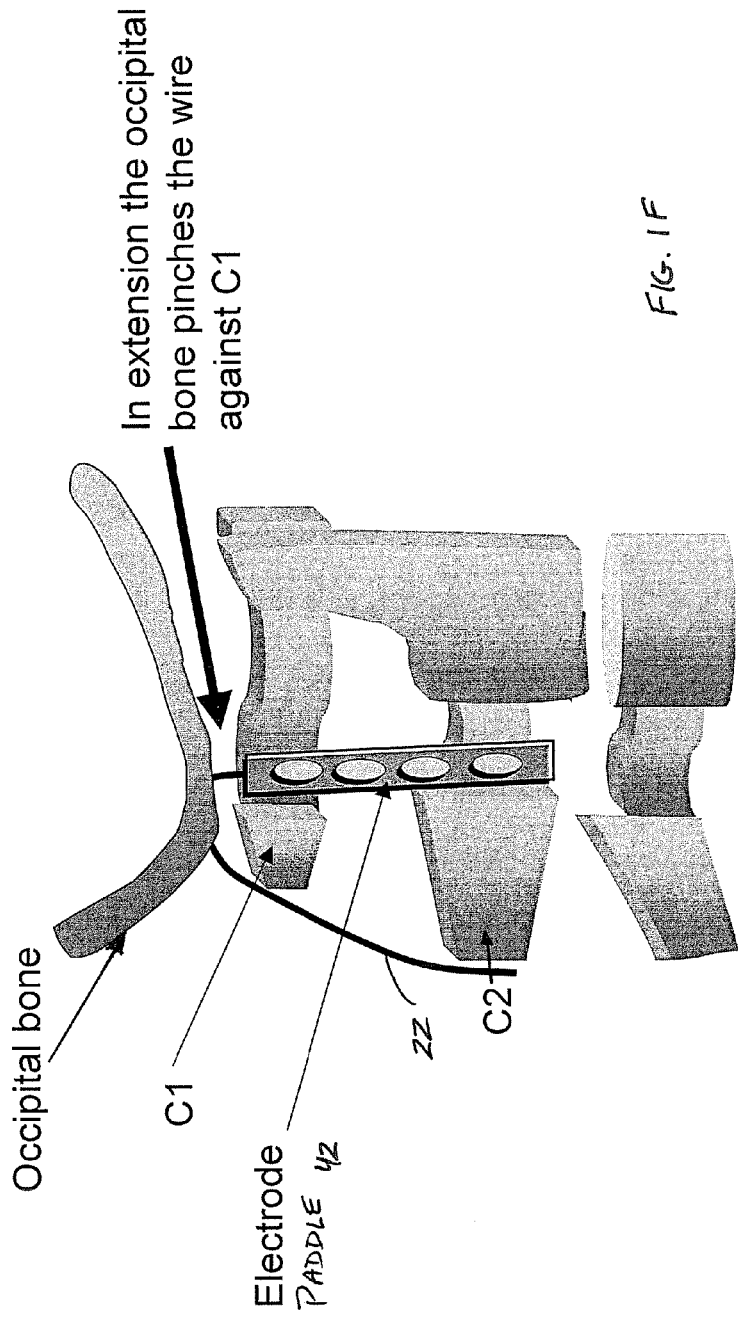

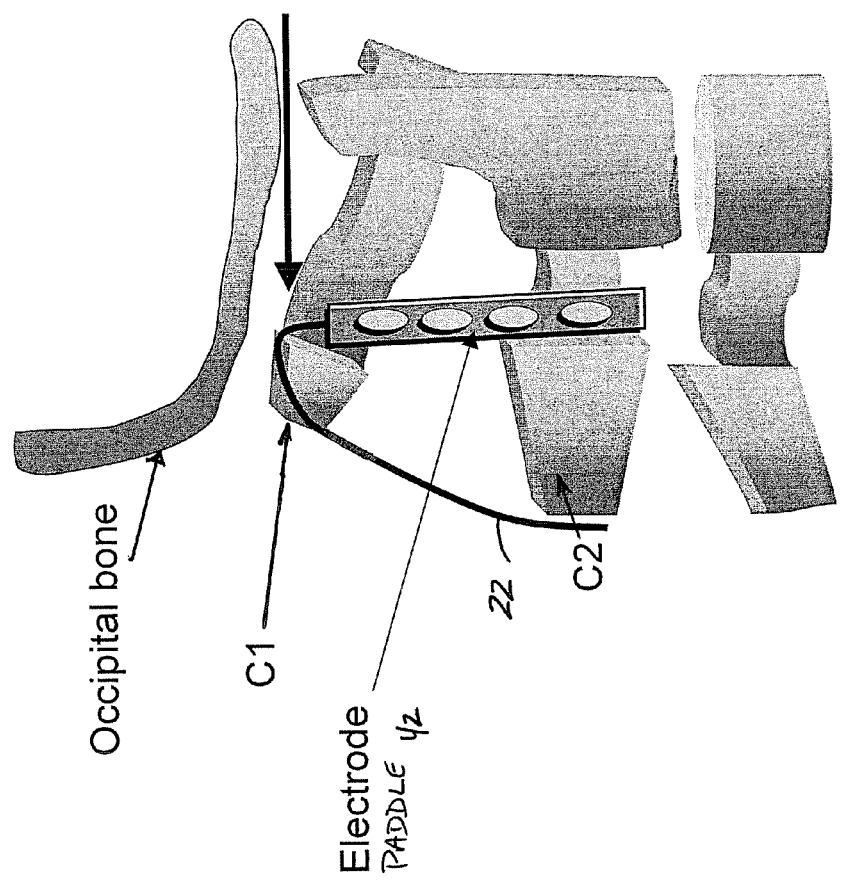

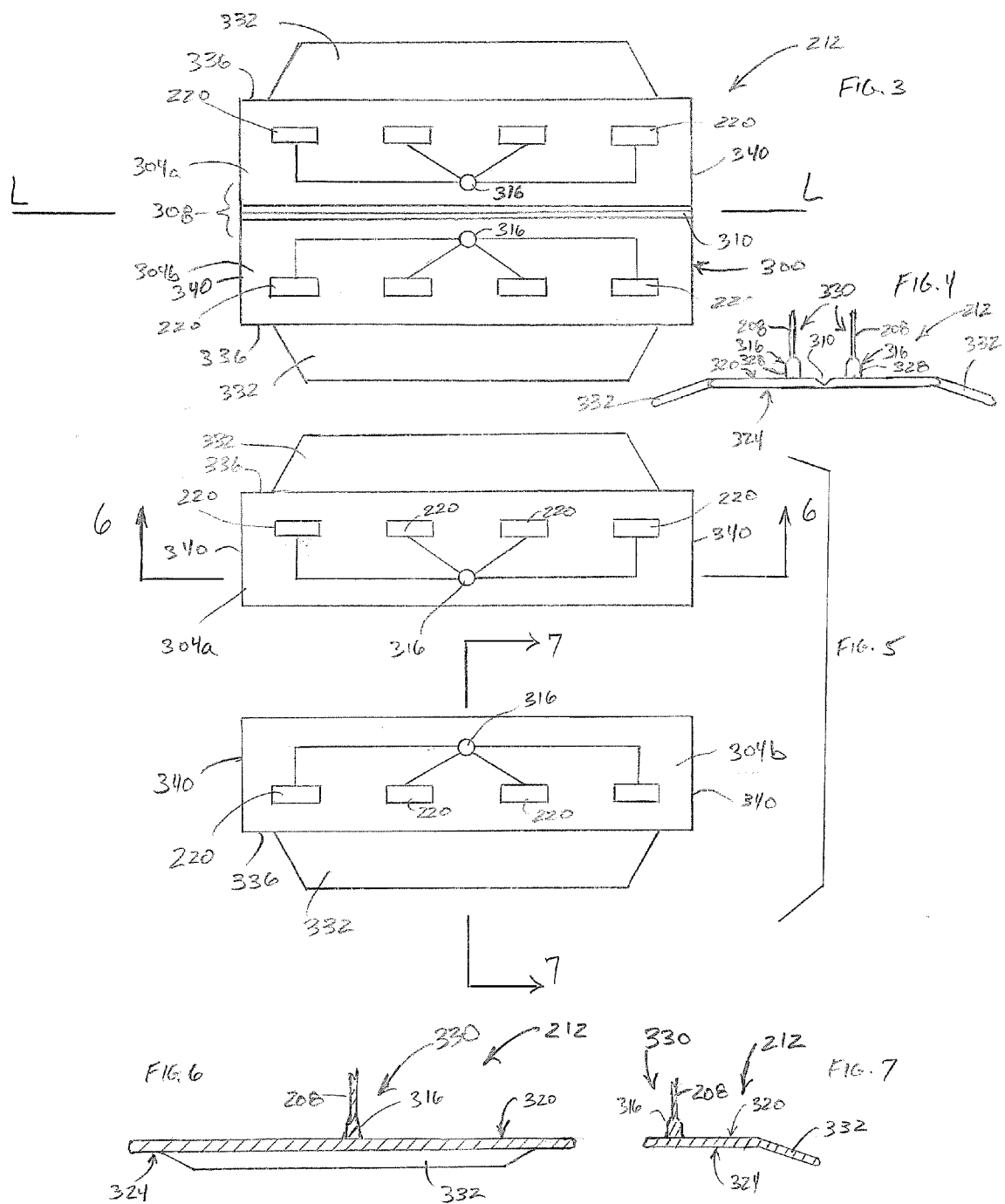

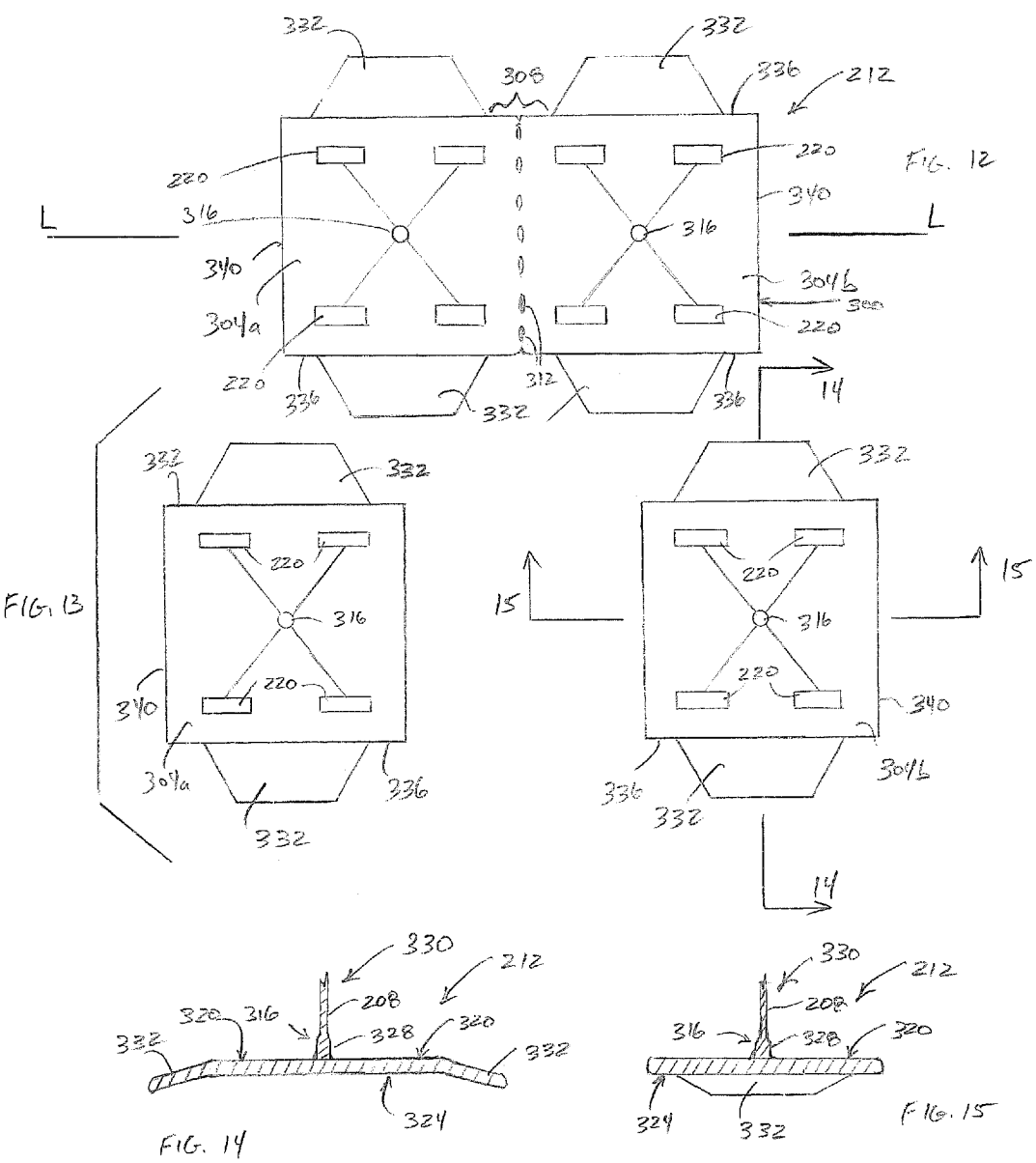

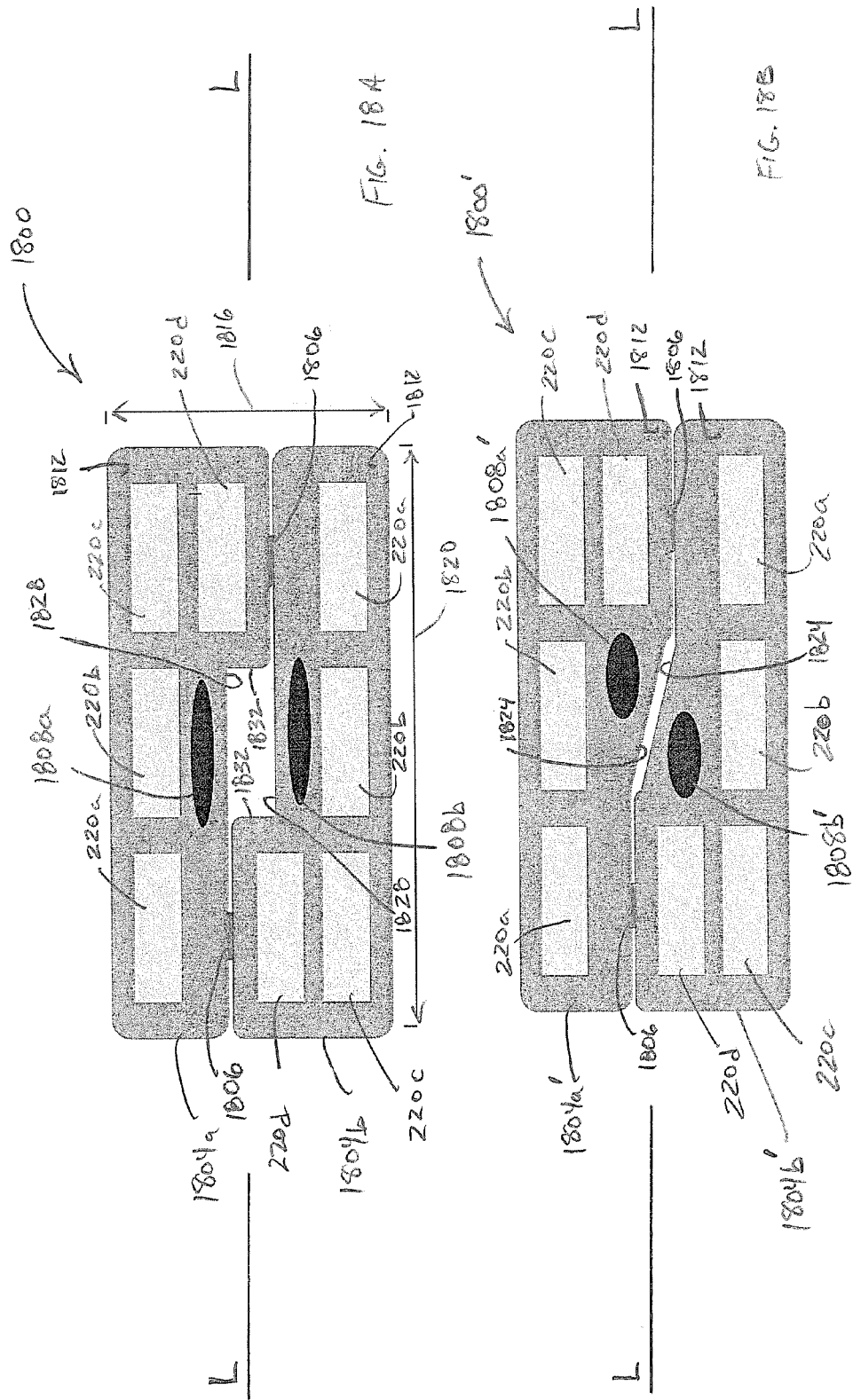

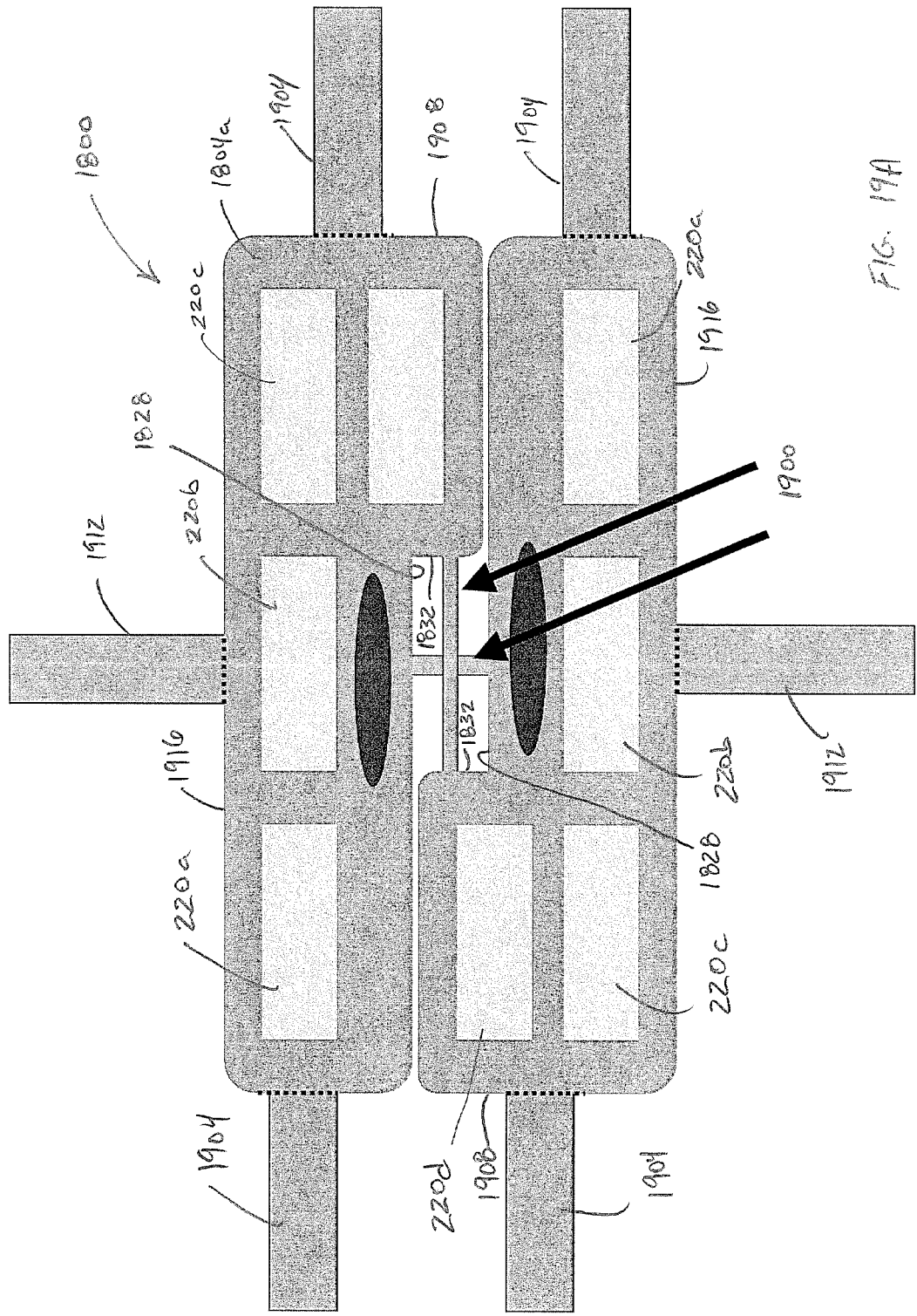

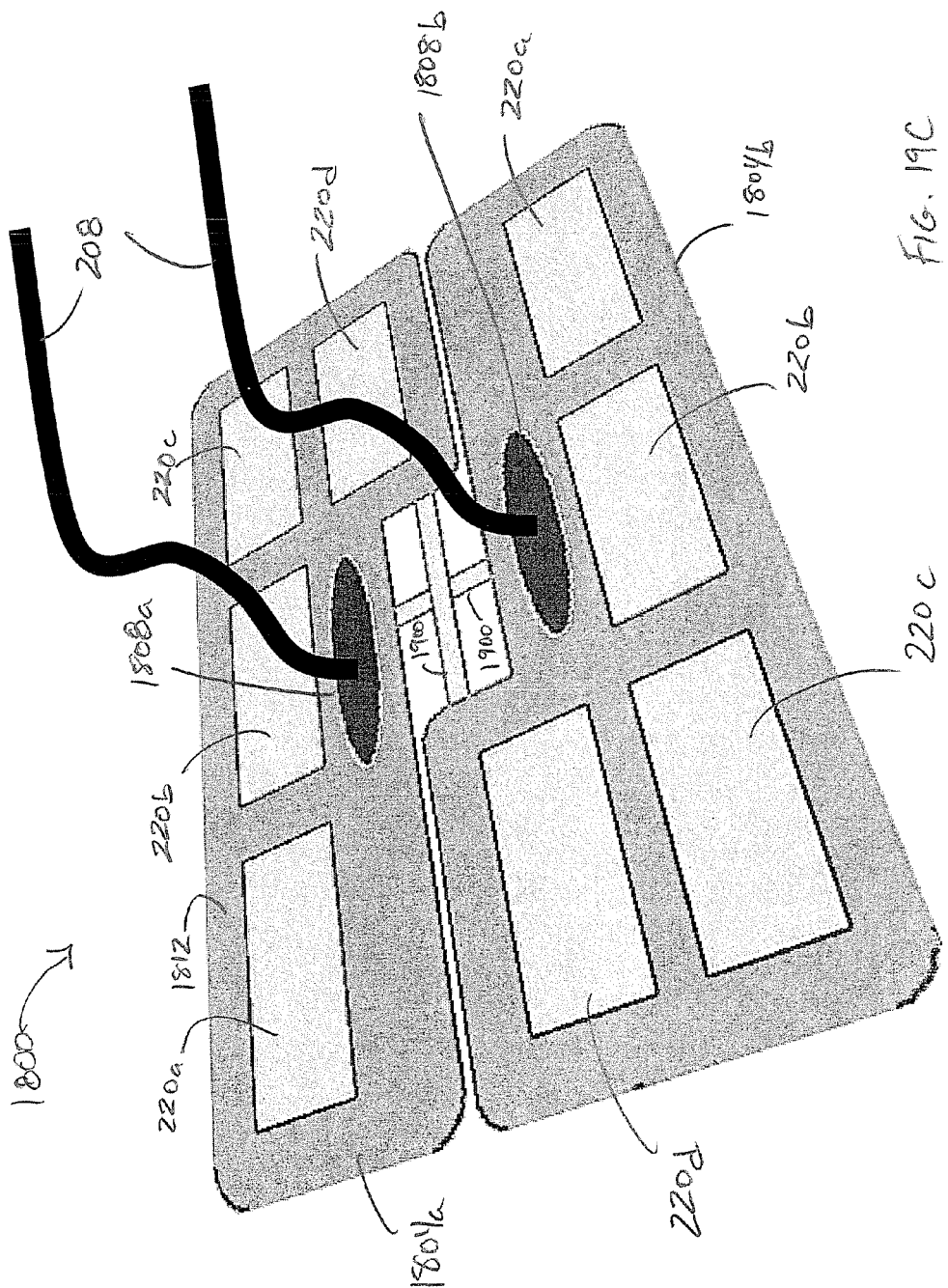

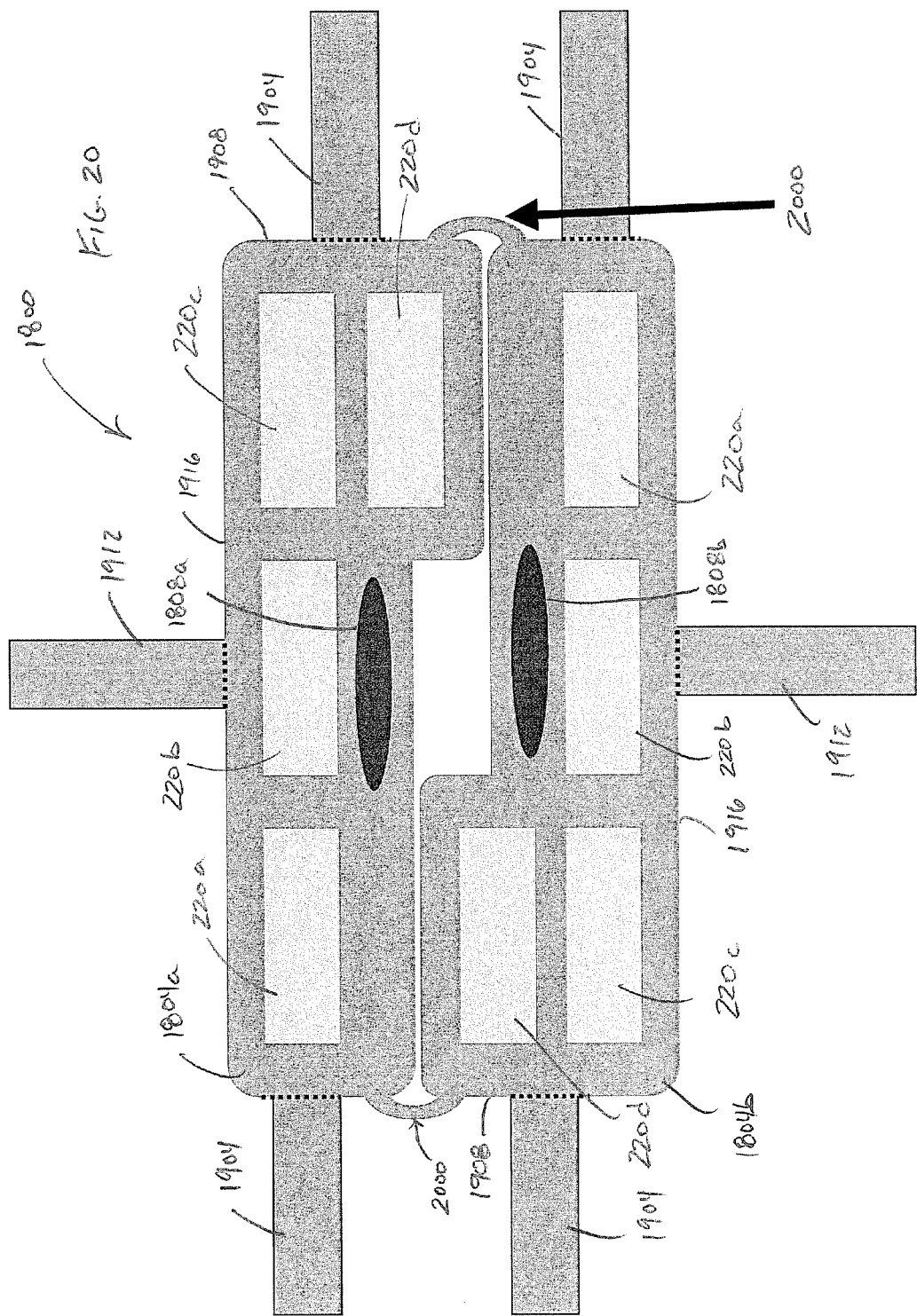

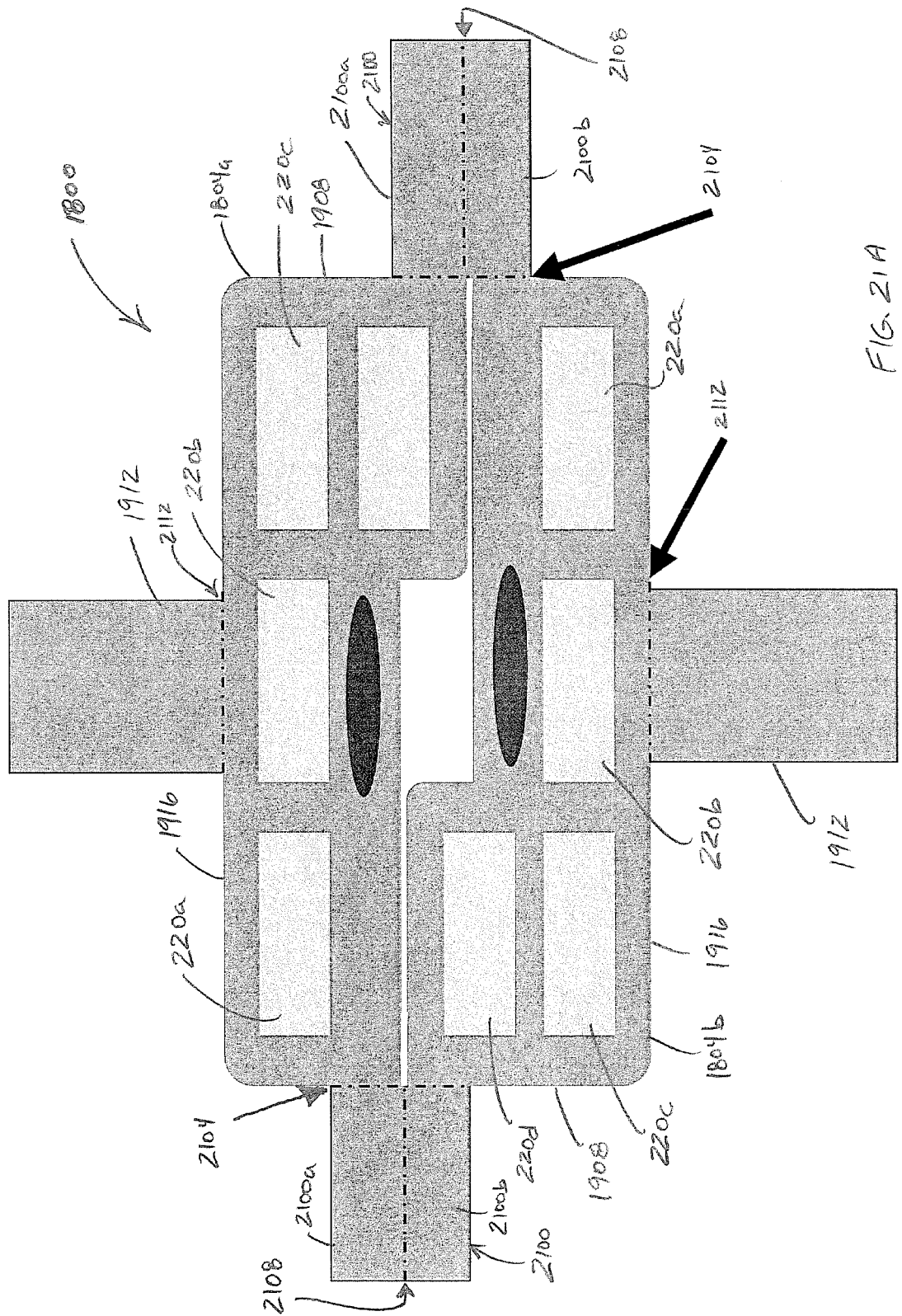

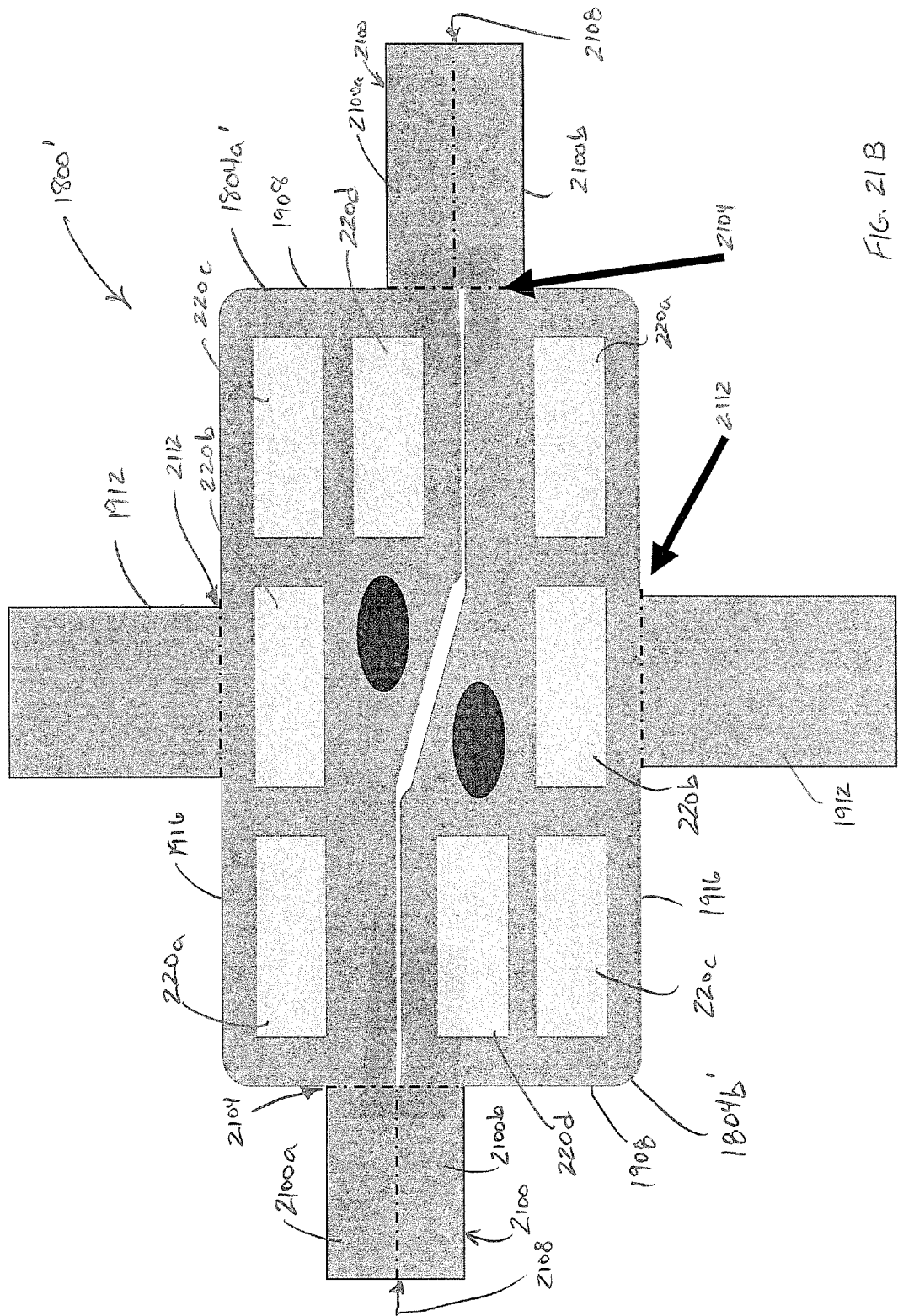

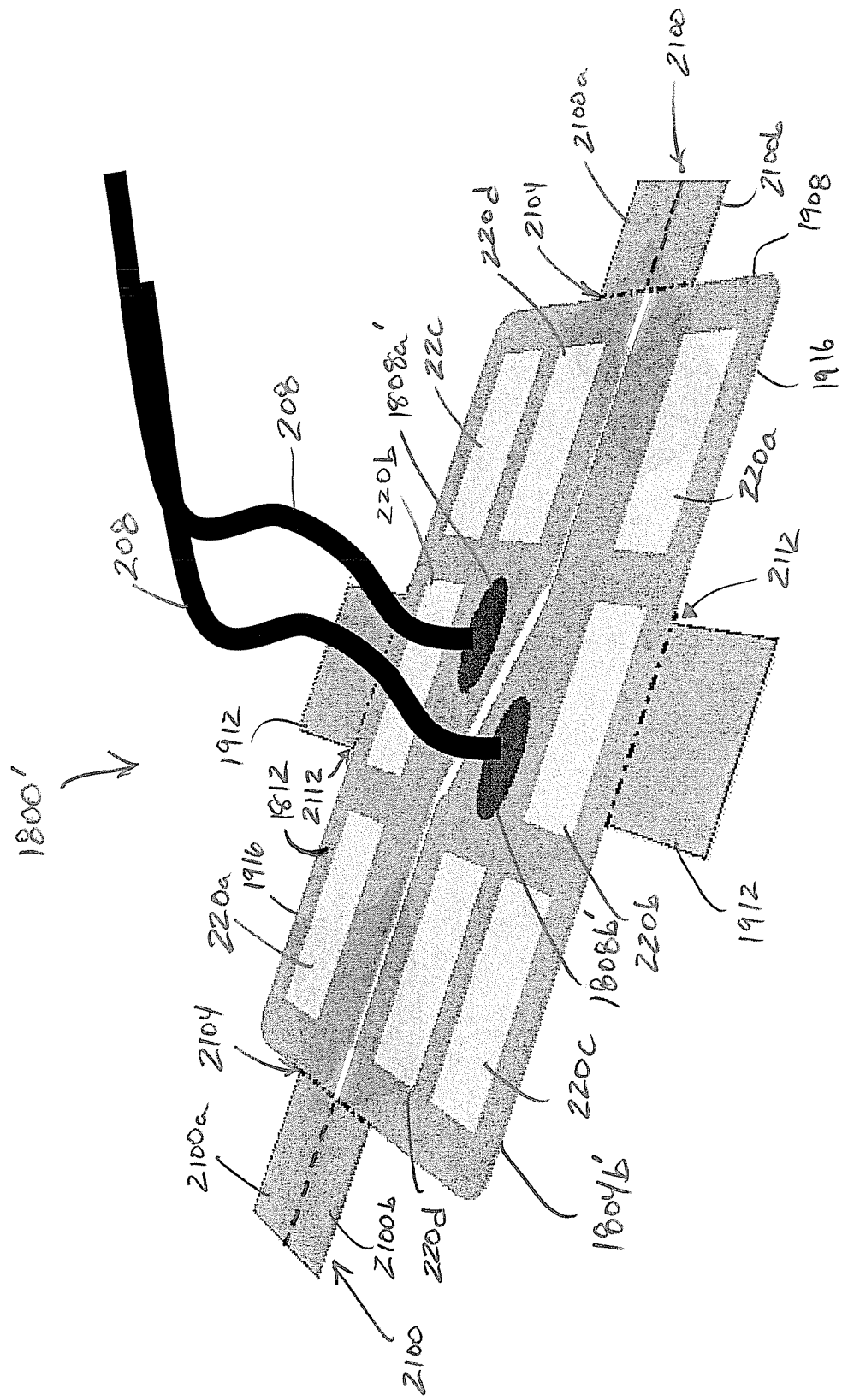

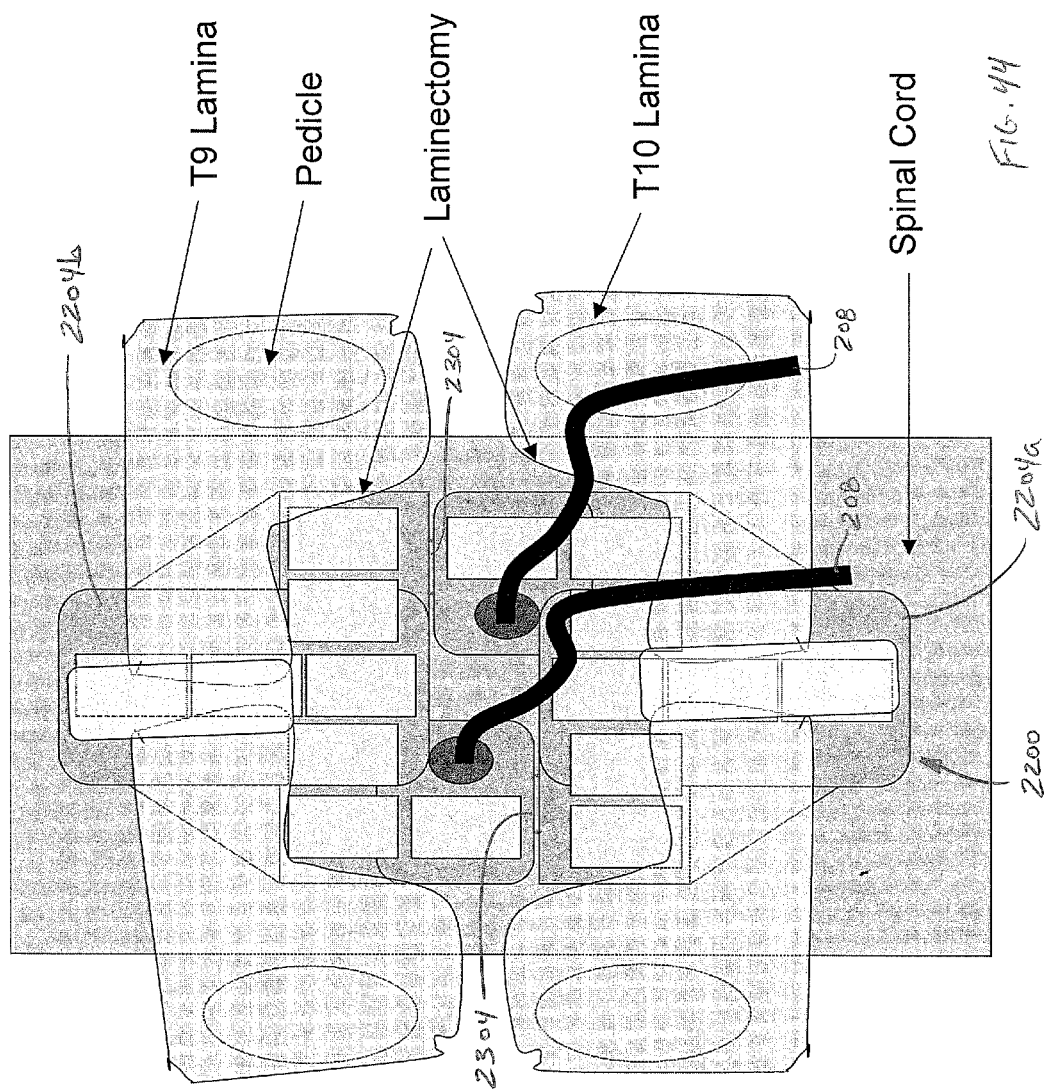

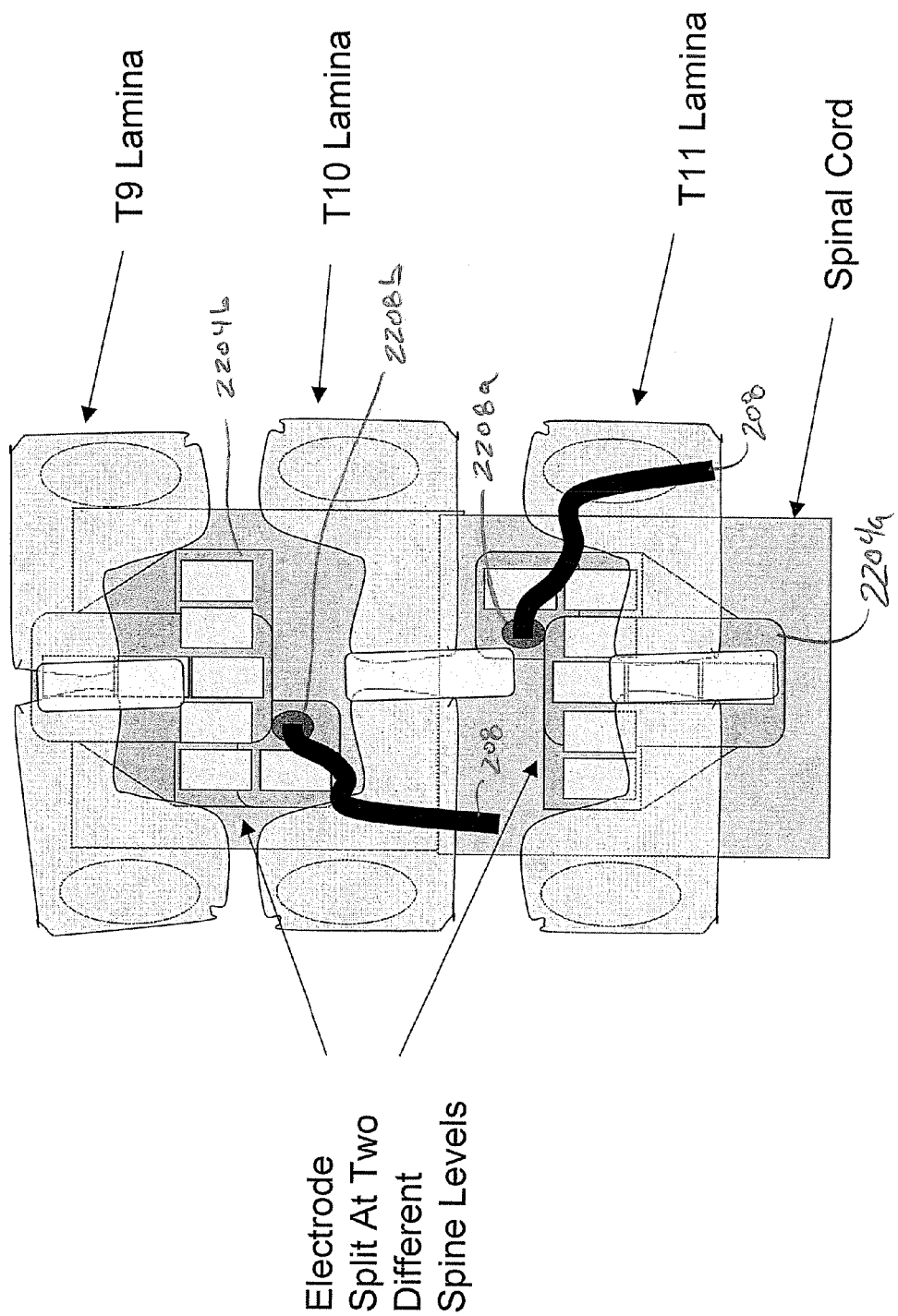

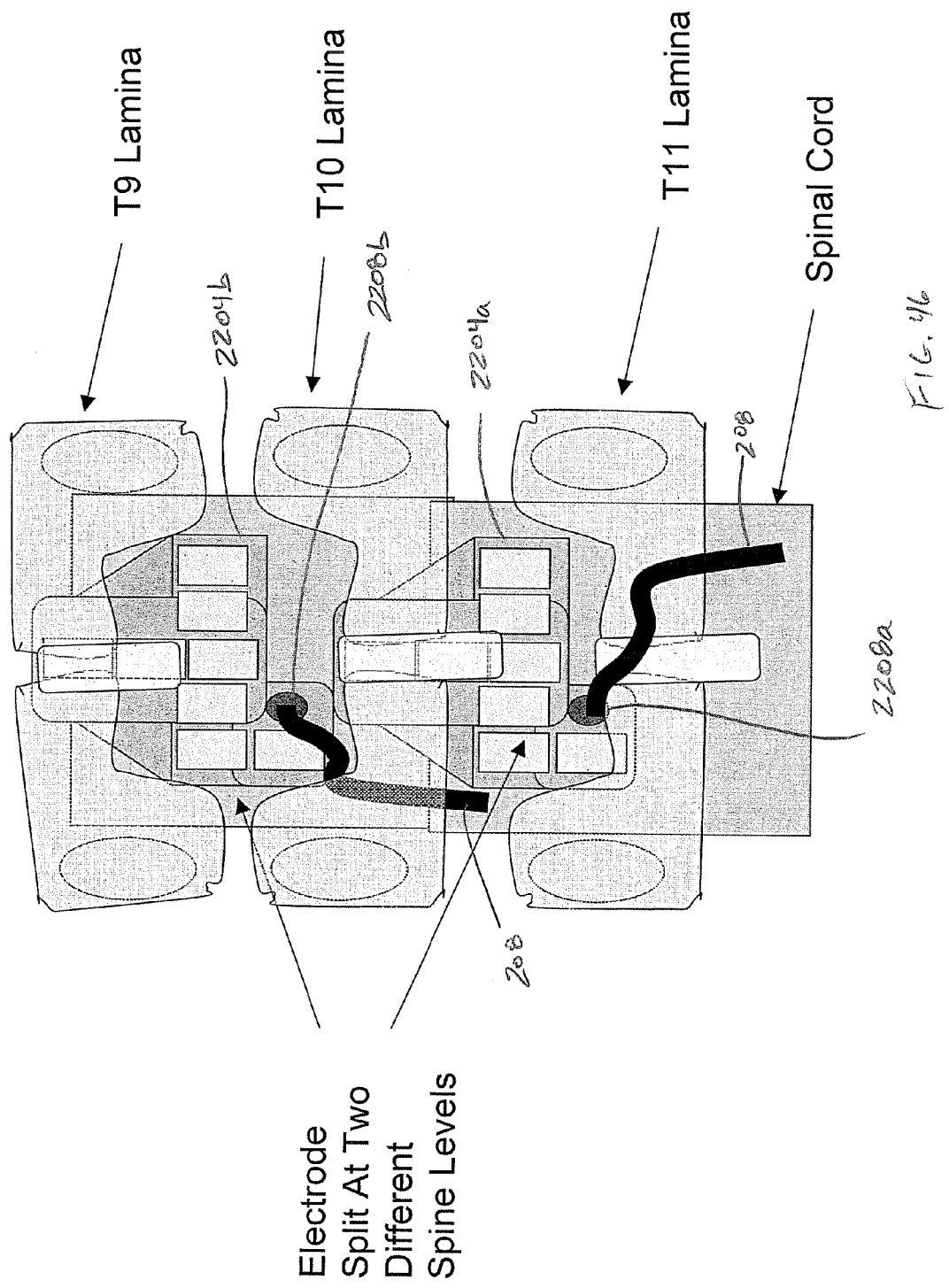

ELECTRODE PADDLE FOR NEUROSTIMULATION

CROSS REFERENCE TO RELATED APPLICATION

The present application is a continuation of U.S. patent application Ser. No. 11/627,337, now issued as U.S. Pat. No. 8,554,337, to Barolat, filed on Jan. 25, 2007, entitled "Electrode Paddle for Neurostimulation," the entire content of which is incorporated herein by reference in its entirety. The present application claims the benefit of the foregoing application.

FIELD

The present invention is related to medical implants, and more particularly, to an implantable electrode for neurostimulation.

BACKGROUND

Electrodes are used to provide electrical stimulation, including electrical stimulation of neural structures in patients suffering from chronic pain. A variety of electrodes and electrode arrays exist for operation in conjunction with a pulse generator. U.S. Patent Application Publication No. 2006/0136008, incorporated herein by reference in its entirety, discloses a number of electrode arrays. For example, and referring to FIG. 1A, an electrode array 10 known in the prior art is shown. The electrode array 10 includes a plurality of electrodes or contacts 14 located at the distal region 18 of a lead 22. Referring to FIG. 1B, an electrode array 10 is located within an electrode paddle 26. The electrode array 10 is formed of a plurality of contacts 14 situated within the relatively flat electrode paddle 26. Referring now to FIG. 1C, two electrode arrays 10 are located within two electrode paddles 26, wherein the leads 22 extend to a common junction 30, and wherein the leads 22 are controlled by a common pulse generator (not shown). For the electrode array shown in FIG. 1C, each electrode array 10 is formed of a plurality of contacts 14 situated within the relatively flat electrode paddle 26.

For the above noted electrode arrays, the electrical lead 22 conveys a pulse of electrical energy from a pulse generator to the electrode arrays 10. In general, the lead 22 enters the electrode array 10 or paddle 26 at a proximal end 34 of the electrode array 10 or paddle 26, where the distal end 38 of the lead 22 is co-planar with the electrode array 10 or paddle 26.

The structure of the existing electrode arrays presents difficulties for a surgeon implanting the electrode paddles within certain areas of the spine because the anatomy of the spine does not necessarily lend itself to implanting an electrode array directly onto the nerves of the spine when the distal end 38 of the lead 22 is also coplanar with the electrode array 10. That is, the spine is three dimensional, and an electrode array 10 cannot necessarily be properly positioned within the spinal canal and on the target neural structures of the spine when the distal end 38 of the electrical lead 22 extends in a coplanar orientation with the electrode paddle 26 containing the electrode array 10.

Referring now to FIG. 1D, a partial side view of an electrode paddle 42 of the prior art is shown implanted at the cervical vertebrae C1-C2 level, and in FIG. 1E, a posterior view of the electrode paddle 42 is shown. For this typical implant configuration, the electrode lead 22 extends from a longitudinal end of the electrode paddle 42 in a caudal direction between the occipital bone and C1. As shown in FIG. 1F, in extension the occipital bone forces the electrode lead 22 downward and pinches the electrode lead 22 against the C1. With repeated motion, the electrode lead 22 experiences stress that can be detrimental to the structural integrity of the electrode wire 22 and its connection to the electrode paddle 42.

To address the spatial limitations resulting from the implant target location and the existing electrode paddle geometries, the surgeon may be forced to compromise in some fashion, such as by: (1) using an alternate and less attractive array configuration; (2) positioning the electrode array near the target location but not exactly at the desired target location; and/or (3) allowing the spine to bend the distal end of the electrical lead at the proximal end of the electrode paddle, thereby risking the structural integrity of the lead connection to the electrode paddle. Thus, it would be advantageous to provide an electrical paddle having an electrical lead configuration that more appropriately accommodates the anatomical features of the spine.

U.S. Pat. No. 3,724,467, incorporated herein by reference in its entirety, discloses an electrode paddle having a lead connection that enters the paddle at an angle of between 15 to 45 degrees. However, this reference fails to disclose a lead connection that connects to the body portion of the electrode paddle along a steep inclination, such as along a substantially perpendicular alignment. Such a perpendicular alignment would be advantageous for implanting at the opening between the L5-S vertebrae.

With regard to use of electrodes to relieve pain, foot pain is notoriously difficult to treat with intraspinal stimulation. If the electrode(s) are placed at the spinal cord level, the stimulation eventually goes away from the foot area because other larger nerve fibers (mostly the thigh) eventually end up capturing most of the stimulation. In order to maintain the stimulation in the foot area, the most precise and reliable target is the L4, L5, S1, S2 nerve roots at the L4-L5 spine level. Electrodes placed on these nerve roots will generally maintain stimulation in the foot. There are several issues with stimulation of the lumbar nerve roots for pain. The target nerves are the lumbar dorsal (sensory) roots that carry sensation. Stimulation of the ventral (motor) roots, which are adjacent of the sensory roots, is greatly undesirable because it produces motor contractions. If an electrode is placed under the lamina, as is necessary with the existing shaped paddle leads, it will exert some degree of pressure on the nerve roots, even if minimal. This amount of pressure is often enough to squeeze the dorsal roots very close to the ventral roots. A significant side effect of the nerve roots coming closer together is that the stimulation will almost inevitably result in stimulating the motor roots preferentially, thereby negating the beneficial effects of the stimulation.

In order to avoid activation of the motor roots, a minimal amount of compression, if any, must be exerted on the nerve roots. In order to accomplish this, no bone should be present dorsal to the electrodes placed on the nerve roots. This presents a difficulty because the existing commercially-available paddle leads rely on the presence of bone dorsally to maintain them in place and prevent their displacement.

Another area that has been problematic for electrode placement is the C1-C2 region of the spine. This area of the spinal cord is an excellent target for stimulation since all of the nerve fibers coming from the upper and lower extremities converge at the C1-C2 level. A physician might, therefore, have the possibility to stimulate all four extremities from one single target. However, two issues make that placement less than ideal with the currently available electrodes. First, since the electrode(s) are placed entering the spine between the occiput and the arch of C1, they are subjected to a significant amount of motion. More particularly, the cranio-cervical junction has one of the highest motion of any spine segment. This puts the electrode at a very high risk of fracturing or possible malfunction. Secondly, the C2 lamina is relatively thick and tends to push the electrode closer to the spinal cord. As a result, the stimulation current more easily spreads, not only to the dorsal columns (a desirable effect), but also to the motor fibers. This will result in undesirable motor contractions that might negate the beneficial effects of the stimulation. Even a thinner electrode might not obviate that problem. Accordingly, the best solution is to have the electrode placed in an area where little or no bone will be present to exert pressure on the electrode.

Yet another area of interest is the T7-T8-T9-T10-T11 area, where a physician may be trying to achieve stimulation of the dorsal columns affecting the lower extremities and the axial lumbar area (which is notoriously difficult to stimulate). Stimulation of the nerves in the T7-T8-T9-T10-T11 levels is often performed to treat pain in the lower back and in the lower extremities. Here again, the configuration of the vertebrae and the location of the target neural structures do not necessarily facilitate ease of treatment using existing commercially-available electrodes.

In addition, while existing electrodes paddles include some material along the boundary of the paddle, the existing electrode paddles do not necessarily include sufficient material for allowing the electrode paddle to be anchored or otherwise stabilized within the environment of the spinal canal. Thus, it would be advantageous to provide an electrode paddle that has structure for allowing the electrode paddle to cooperate with the structure of the vertebrae of the spine for maintaining the position of the electrode paddle within the spinal canal once it is implanted, whether or not a laminectomy has been performed.

Another difficulty associated with electrode arrays and electrode paddles of the prior art is that they are generally provided in a one-piece configuration and do not readily permit the surgeon to modify their shape to accommodate the physical attributes of the patient during surgery. Accordingly, it would be advantageous to provide an electrode paddle that accommodated modification during the surgical procedure to allow the surgeon to modify the shape and/or orientation of the electrode array to suit the patient's needs.

SUMMARY

Various embodiments of the present invention address the shortcomings of the prior art. It is to be understood that the present invention includes a variety of different versions or embodiments, and this Summary is not meant to be limiting or all-inclusive. This Summary provides some general descriptions of some of the embodiments, but may also include some more specific descriptions of certain embodiments.

In at least some embodiments of the present invention, an electrode paddle is provided for allowing the distal end of an electrode paddle to be positioned proximate an edge of a vertebra. More particularly, in at least some embodiments of the present invention, the lead connection from the electrode lead to the electrode paddle includes a substantially perpendicular orientation. In addition, in at least some embodiments of the present invention an electrode paddle is provided that includes a structure for stabilizing the electrode paddle along the spinal canal or nerve branches associated with the spinal canal. More particularly, in at least some embodiments of the present invention, the electrode paddle includes one or more flanges that extend from an edge of the electrode paddle. In at least some embodiments of the present invention an electrode paddle is provided that can be separated into a plurality of paddle sections. Embodiments of the present invention may also include an electrode paddle having a plurality of paddle sections that can be separated, wherein the paddle sections each include a plurality of contacts. In at least some embodiments of the invention, the plurality of contacts are positioned asymmetrically on each paddle section.

It is also an aspect of the present invention to provide an electrode paddle that can be used in combination with other previously implanted pulse generators, electrode leads and electrode arrays, where the lead connection entering the existing electrode array has been broke or damaged. The current invention allows a surgeon to replace the lead and electrode array to provide a more suitable electrode array with structural features that prevent or otherwise mitigate spatial problems associated with the broke or damaged electrode array.

The present invention includes a method of assembling a neurostimulation system that is implantable in a patient to stimulate a plurality of nerves/neural fibers. The method includes providing an implantable pulse generator and an implantable lead. In addition, the method includes providing an electrode paddle having a plurality of separable paddle sections, wherein the paddle sections each include a plurality of contacts that are not linearly aligned. The electrode paddle can be electrically connected or interconnectable to the implantable pulse generator by the implantable lead.

In accordance with embodiments of the present invention, an implantable system for implanting into a patient to stimulate one or more neural structures is provided, the implantable system comprising: (a) a way of generating an electrical pulse; (b) a way of transmitting the electrical pulse; and (c) a device for holding a plurality of contacts wherein the plurality of contacts are adapted to be in electrical communication with the transmitting device and wherein the plurality of contacts are configured to carry the electrical pulse to stimulate the one or more neural structures. The device for holding the contacts preferably includes a way of being divided wherein the device for holding is divisible into a plurality of sections, wherein at least two contacts located in each section are aligned along a first axis and at least two additional contacts in each section are aligned along a second axis, and wherein the first axis and the second axis are transverse to one another. In accordance with embodiments of the present invention, the system includes a lead connection for perpendicularly interconnecting an electrical lead to the device that holds the electrodes. The device for holding the contacts may include a body and at least one flange, wherein the flange extends beyond a longitudinal end or lateral side of the body of the device that holds the contacts.

It is noted that the present invention has application to systems that are implantable within humans, and also has application to veterinary medicine, wherein the devices and methods described herein may be used in association with treating, for example, animals, such as horses.

It is also an aspect of the present invention to provide a method of implanting an electrode array. Thus, in accordance with embodiments of the present invention, a method of installing a neurostimulation system in a patient is provided. The method includes:

(a) making an incision in a first tissue of the patient, the incision for placement of a pulse generator;

(b) making an incision in a second tissue of the patient, the incision for placement of at least one electrode paddle, wherein the electrode paddle includes a plurality of paddle sections, and wherein at least one paddle section includes a plurality of contacts that are configured asymmetrically.

Various embodiments of the present invention are set forth in the attached figures and in the detailed description of the invention as provided herein and as embodied by the claims. It should be understood, however, that this Summary does not contain all of the aspects and embodiments of the present invention, is not meant to be limiting or restrictive in any manner, and that the invention as disclosed herein is and will be understood by those of ordinary skill in the art to encompass obvious improvements and modifications thereto.

Additional advantages of the present invention will become readily apparent from the following discussion, particularly when taken together with the accompanying drawings.

BRIEF DESCRIPTION OF THE DRAWINGS

FIG. 1D is a partial side elevation view of a electrode paddle of the prior art, wherein the electrode paddle is shown implanted proximate the C1 and C2 cervical vertebrae, wherein the paddle has been inserted in a caudal direction entering the spine between the occipital bone and C1;

FIGS. 1F and 1G are additional views of the electrode paddle of FIG. 1D where movement of cervical vertebrae has occurred;

FIG. 3 is a plan view of an electrode paddle in accordance with embodiments of the present invention;

FIG. 4 is a side elevation view of the device shown in FIG. 3;

FIG. 5 is a plan view of the device shown in FIG. 3 after it has been divided;

FIG. 6 is a cross-sectional view taken along line 6-6 as shown in FIG. 5;

FIG. 7 is a cross-sectional view taken along line 7-7 as shown in FIG. 5;

FIG. 12 is a plan view of an electrode paddle in accordance with embodiments of the present invention;

FIG. 13 is a plan view of the device shown in FIG. 12 after it has been divided;

FIG. 14 is a cross-sectional view taken along line 14-14 as shown in FIG. 13;

FIG. 15 is a cross-sectional view taken along line 15-15 as shown in FIG. 13;

FIGS. 18A and 18B are plan views of electrode paddles in accordance with at least one embodiment of the present invention;

FIG. 19A is plan view of an electrode paddle in accordance with at least one embodiment of the present invention;

FIGS. 19B and 19C are perspective views of an electrode paddle in accordance with at least one embodiment of the present invention;

FIG. 20 is plan view of an electrode paddle in accordance with at least one embodiment of the present invention;

FIGS. 21A and 21B are plan views of electrode paddles in accordance with at least one embodiment of the present invention;

FIG. 21C is a perspective view of the electrode paddle shown in FIG. 21B;

FIGS. 44-46 are posterior views of the T9-T11 thoracic vertebrae with exemplary uses of embodiments of the present invention.

The drawings are not necessarily to scale.

DETAILED DESCRIPTION

Embodiments of the present invention are directed to an implantable electrode paddle for use in a neurostimulation system. Embodiments of the present invention may include a dorsally-projecting lead that allows all of the edges of the electrode paddle to be situated near a vertebral body. Embodiments of the may also include one or more flanges for cooperating with a vertebral body and thereby stabilizing the electrode paddle. In addition, embodiments of the present invention may also include features to allow an electrode paddle to be divided during surgery. It is also an aspect of the present invention to provide an electrode paddle that can be used in combination with other previously implanted pulse generators, electrode leads and electrode arrays, where the lead connection entering the existing electrode array has been broke or damaged. Embodiments of the present invention are suitable for allowing a surgeon to replace an existing lead and electrode array to provide a more suitable electrode array with structural features that prevent or otherwise mitigate spatial problems associated with a broken or damaged lead or electrode array. As discussed below, still other embodiments of the present invention are directed at methods of using the electrode paddle.

Figure 2:
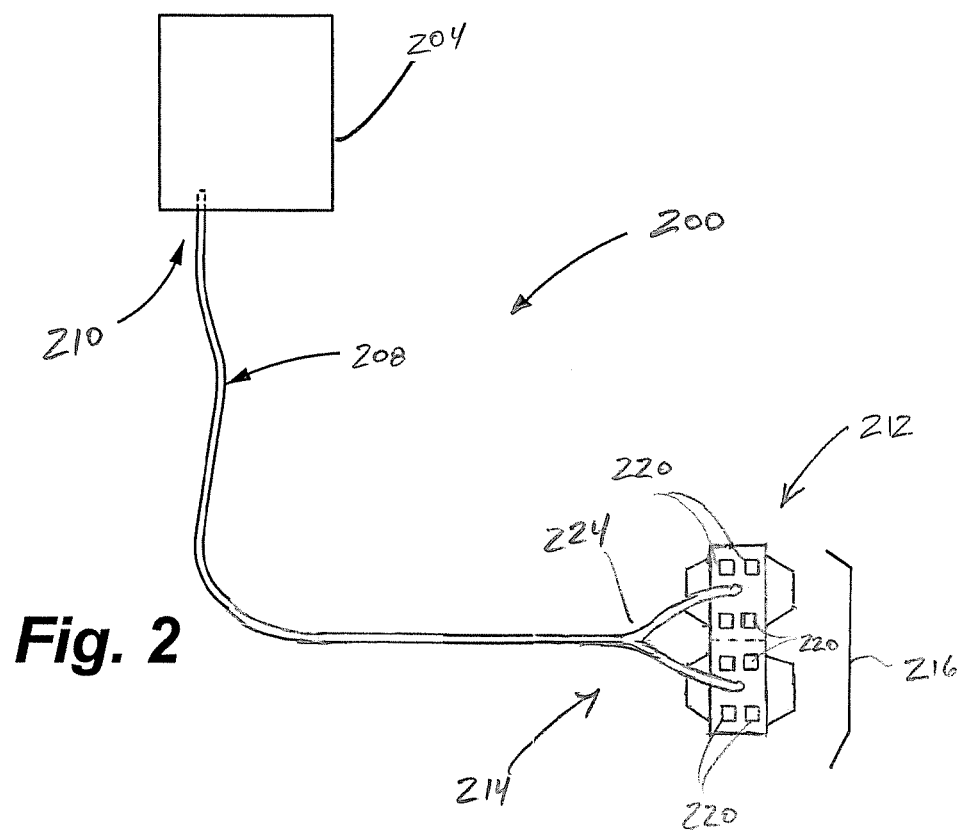
FIG. 2 is a plan view of an electrical stimulation system in accordance with embodiments of the present invention.

Referring now to FIG. 2, and in accordance with embodiments of the present invention, an electrical stimulation system 200 is shown. The electrical stimulation system 200 comprises an implantable pulse generator 204, a lead body 208, and an electrode paddle 212. The lead body 208 includes a proximal end 210 that is connected (or is interconnectable) to the implantable pulse generator 204. The distal end 214 of the lead body 208 includes the electrode paddle 212 comprising an electrode array 216 that includes a plurality of electrical contacts 220. The lead body 208 may include a common junction 224 where the lead bodies 208 to the paddle sections join.

Figure 8:
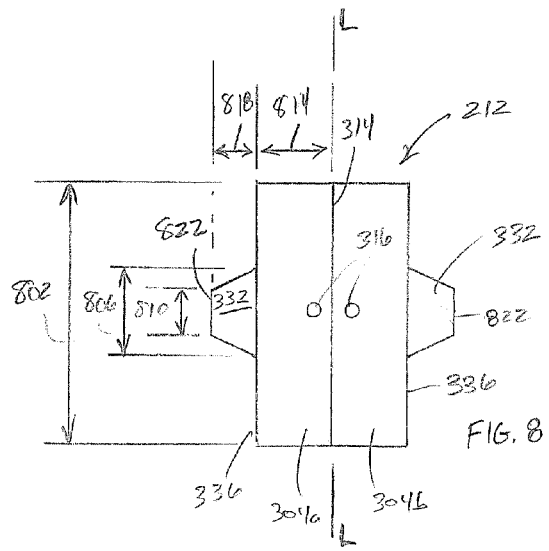
FIG. 8 is plan view of an electrode paddle in accordance with at least one embodiment of the present invention.

Referring now to FIG. 3, additional detail of an embodiment of an electrode paddle 212 is shown. In at least one embodiment of the invention, the electrode paddle 212 comprises a paddle body 300 that includes a plurality of paddle sections 304a and 304b, wherein the paddle sections 304a, 304b are initially connected to one another. More particularly, the electrode paddle 212 includes a webbing portion 308 that is configured for dividing the electrode paddle 212 into a plurality of sections. In accordance with at least some embodiments of the invention, and as best seen in FIG. 4, the webbing 308 comprises a groove 310 oriented along the longitudinal axis L-L of the electrode paddle 212. The groove 310 facilitates separation of the paddle sections 304a and 304b if the surgeon decides to divide the electrode paddle 212 prior to or during the course of the implant procedure. Other alternative structure may also be used to facilitate ease of dividing the electrode paddle 212. For example, a series of perforations 312 may be used (as shown in FIG. 12) for facilitating separation of the paddle sections 304a and 304b. Other alternative configurations are also within the scope of the invention. For example, as seen in FIG. 8, the webbing may have a score 314 for facilitating separation of the paddle sections. Alternatively, the webbing 308 may be imperforated, but readily capable of being cut by the surgeon or his or her staff. Thus, a variety of ways are possible to configure the electrode paddle 212 for division into a number of separate paddle sections, and such possible configurations are within the scope of the present invention. The webbing 308 serves not only as an area of the electrode paddle 212 for separating one paddle section from another, but the webbing also serves to both isolate and electrically insulate the contacts 220 of one paddle section from the electrodes of the one or more other paddle sections, such as by isolating and insulating the contacts 220 of paddle section 304a from the contacts 220 of paddle section 304b. Accordingly, the material forming the body of the paddle around the contacts 220 is an electrically insulating material, and the webbing 308 is preferably formed of an electrically insulating material. Although two paddle section 304a and 304b are shown in several of the figures, it is to be understood that the electrode paddles may comprise more than two paddle sections, such as three paddle sections, four paddle sections, etc.

Referring now to FIG. 5, there is shown the electrode paddle 212 of FIG. 3 divided into the separate paddle sections 304a and 304b. As can be seen in FIG. 5, the electrode paddle 212 has been divided along its longitudinal axis L-L. However, the electrode paddle 212 could be divided into separate paddle sections that are not equal in size.

Referring now to FIGS. 3 and 5-7, and in accordance with embodiments of the present invention, the electrode paddle 212 includes a plurality of lead connections 316, wherein the lead connections 316 are spaced apart from the edges of the electrode paddle 212. More particularly, the lead connections 316 do not connect to the electrode paddle 212 at a lateral side 336 or longitudinal end 340 of the electrode paddle 212. Instead, the lead connection 316 is non-planar with the electrode paddle 212. That is, the lead connection 316 enters the paddle from the dorsal or back side 320 of the electrode paddle 212 relative to the front side 324, where the front side 324 corresponds to the surface of the electrode paddle 212 for contacting the contacts 220 with the intended neural structures of the patient. The lead connections 316 may include a reinforced portion or sheath 328 at the distal end 330 of the lead 208, wherein the sheath 328 serves to protect the wires or filaments within the lead 208 from being damaged where there is a bend in the wiring from the lead 208 to the electrode paddle 212.

Referring to FIGS. 3-7, and in accordance with embodiments of the present invention, the electrode paddle 212 includes one or more flanges 332 along it sides. For the electrode paddle 212 shown in FIGS. 3-7, the flanges 332 are located along the lateral sides 336. However, it is to be understood that the one or more flanges 332 could also be located along one or both of the longitudinal ends 340 of the electrode paddle 212. The flanges are not necessarily used to suture the electrode paddle 212 to the tissue of the patient, but serve to hold the electrode paddle 212 in place by positioning the flange in contact with an anatomical structure, such as the lamina of a vertebra, where the vertebra holds the flange, and therefore the electrode paddle 212 in place. It is further noted that sutures may also be used to hold the electrode paddle in place.

In accordance with embodiments of the present invention, an electrode paddle 212 may comprise only one flange 332. For example, an electrode paddle 212 may comprise a flange 332 located on a lateral side 336, but not on the other lateral side 340. Such a configuration has application where the flange on the lateral side 336 is used to secure the electrode paddle under a portion of one or more vertebra, but a flange is not needed on the other lateral side 340.

In accordance with embodiments of the present invention, the flanges 332 comprise an extension of the material forming the electrode paddle 212, although a different type of material may be used for the flanges 332. In use, the surgeon positions the electrode paddle 212 such that the contacts 220 of the electrode paddle are in electrical communication with the targeted neural structures. The surgeon also positions or tucks the one or more flanges 332 under the adjacent vertebra, or otherwise positions the flanges to assist in stabilizing the location of the electrode paddle 212. Thus, the flanges 332 serve to hold or assist in holding the electrode paddle 212 in place. The flanges 332 may be trimmed by the surgeon during the implantation procedure to further customize the flanges 332 to fit the physical needs of the patient.

Referring now to FIG. 8, and in accordance with embodiments of the present invention, an electrode paddle 212 is shown that includes a first paddle section 304a and a second paddle section 304b with one flange 332 located on each of the lateral sides 336. As depicted in FIG. 8, the electrode paddle 212 has a paddle length 802 and the flange 332 has an outer flange length 806 and an inner flange length 810, where the inner flange length 810 is measured at the junction between the electrode paddle 212 and the flange 332. In accordance with embodiments of the present invention, flange 332 is centered along the paddle length 802. In addition, by way of example and not limitation, the inner flange length 806 is about 33% of the paddle length 802, and the outer flange length 810 is about 50% of the length of the inner flange length 806. Although shown in other drawings and described further below, other ratios from those given above are within the scope of the present invention.

Referring still to FIG. 8, each paddle section also has a paddle section width 814, and in at least some embodiments of the invention, the widths of the various paddle sections are substantially equal, although mixed width sizes are also within the scope of the present invention. The flange 332 has a flange width 818 as measured between the lateral side 336 of the paddle section 304 and the outer lateral edge 822 of the flange 332. By way of example and not limitation, the flange width 818 is between about 50 to 75% of the paddle section width 814, and more preferably, the flange width 818 is between about 55 to 70% of the paddle section width 814, and more preferably yet, the flange width 818 is between about 58 to 65% of the paddle section width 814.

Figure 9:
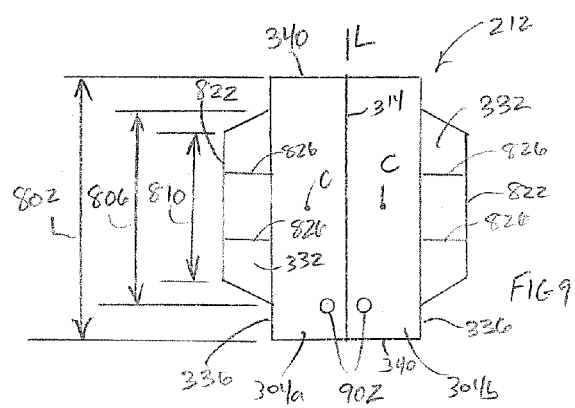
FIG. 9 is plan view of an electrode paddle in accordance with at least one embodiment of the present invention.

Referring now to FIG. 9, an electrode paddle 212 is shown wherein the flanges 332 comprise a relatively longer length than the flanges 332 illustrated in FIG. 8. For the electrode paddle 212 shown in FIG. 9, the inner flange length 806 is about 75% of the paddle length 802, and the outer flange length 810 is about 75% of the length of the inner flange length 806. Such longer flanges 332 may include structure to allow the flange 332 to more easily accommodate the anatomy where it is intended to be located. By way of example and not limitation, the flange 332 may include one or more thinned sections and/or grooves 826 to allow the flange to bend more easily along its longitudinal length. The paddle sections 304 may also include structure to allow some articulation of the paddle section 304. Such articulation structure reduces the tendency of the flange 332 and/or the paddle section 304 to move due to twisting or other motion by the patient after the electrode paddle 212 has been implanted.

Still referring to FIG. 9, consistent with the lead connections 316 shown in FIG. 3 and FIG. 8, the lead connections 902 are shown spaced apart from the lateral sides 336 of the electrode paddle 212, and spaced apart from the longitudinal ends 340 of the electrode paddle 212. However, the lead connections 902 shown in FIG. 9 are not located at the longitudinal center of the electrode paddle 212. Rather, the lead connections 902 are offset longitudinally from the longitudinal center C of the electrode paddle 212. The longitudinally offset lead connections 902 allow a larger portion of the electrode paddle 212 to be placed under the lamina of a vertebra, while still allowing the lead 208 to enter the electrode paddle 212 from an orientation transverse to the substantially planar top surface 320 of the electrode paddle 212.

Figure 10:
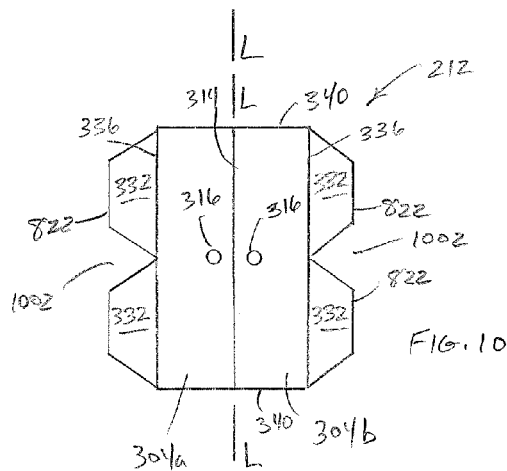
FIG. 10 is plan view of an electrode paddle in accordance with at least one embodiment of the present invention.

Referring now to FIG. 10, an electrode paddle 212 in accordance with embodiments of the present invention is shown, wherein the electrode paddle 212 includes a plurality of flanges 332 along each of its lateral sides 336. As depicted in FIG. 10, the flanges 332 include a gap 1002 along their outer lateral edge 822 that extends to the lateral sides 336 of the electrode paddle 212.

Figure 11:
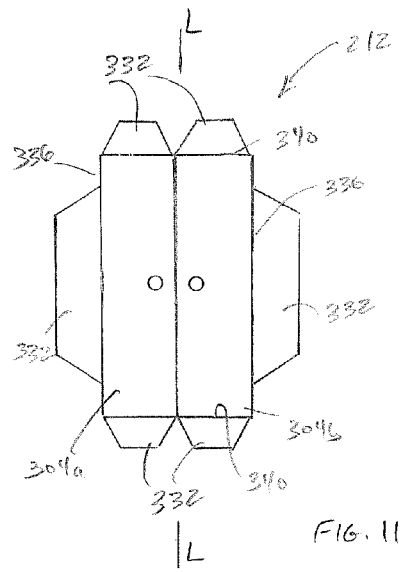
FIG. 11 is plan view of an electrode paddle in accordance with at least one embodiment of the present invention.

Referring now to FIG. 11, an electrode paddle 212 in accordance with embodiments of the present invention is shown, wherein the electrode paddle 212 includes a plurality of flanges 332, including flanges 332 along the longitudinal ends 340 of the electrode paddle.

Referring now to FIG. 12, an electrode paddle 212 in accordance with embodiments of the present invention is shown, wherein the electrode paddle 212 includes a plurality of paddle sections 304 that may be separated along a webbing 308, where the webbing is transverse to the longitudinal axis L-L of the electrode paddle 212. In comparing the electrode paddle 212 of FIG. 3 to the electrode paddle 212 of FIG. 12, it is apparent that the paddle sections 304 of the electrode paddle 212 of FIG. 3 are separable along an axis substantially parallel to the longitudinal axis L-L of the electrode paddle 212, while the paddle sections 304 of the electrode paddle 212 of FIG. 12 are separable along an axis substantially perpendicular to the longitudinal axis L-L of the electrode paddle 212. FIG. 13 shows the electrode paddle 304a and 304b after they have been separated along perforations 312.

Referring now to FIGS. 14 and 15, cross-sections through paddle section 304b are shown. These cross sections further illustrate the substantially perpendicular alignment of the lead connection 316 to the top surface 320 of the electrode paddle 212. FIGS. 14 and 15 also illustrate that the flanges 332 may be angled relative to the substantially flat nature of the paddle body 300 of the electrode paddle 212.

Figure 16:
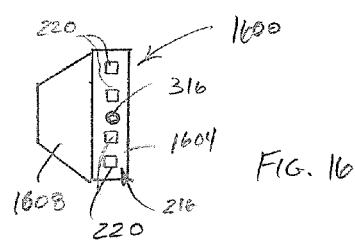
FIG. 16 is plan view of an electrode paddle in accordance with at least one embodiment of the present invention.

Referring now to FIG. 16, an electrode paddle 1600 is shown that comprises a paddle body 1604 that is unitary and does not include structure for separation into smaller paddle sections. However, the electrode paddle may comprise a flange 1608. In accordance with at least some embodiments of the present invention, the flange 1608 has a surface area larger than the surface area of the paddle body 1604. The relative size of the flange 1608 allows for a relatively small electrode array 216 to be held in place by a vertebra. In addition, a substantially perpendicular oriented lead connection 316 may be used to allow the edges of the electrode array to be position near a vertebra while not causing a spatial problem between the lead and the sides of the electrode paddle in relation to the patients anatomical structures at the implant site.

Figure 17:
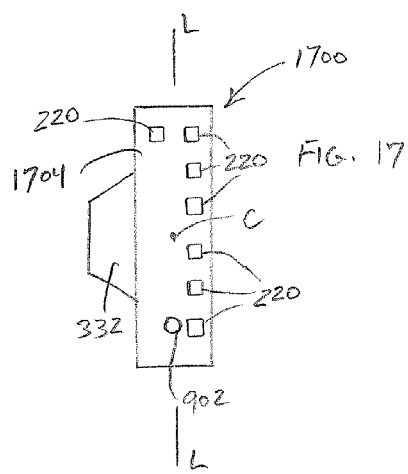
FIG. 17 is plan view of an electrode paddle in accordance with at least one embodiment of the present invention.

Referring now to FIG. 17, an electrode paddle 1700 is shown that comprises a paddle body 1704 that is unitary and does not include structure for separation into smaller paddle sections. However, the electrode paddle 1700 comprises a flange 332 and a longitudinally offset lead connection 902. In addition, the electrode paddle 1700 may include a plurality of electrical contacts (also referred to herein as "contacts") 220 wherein the contacts 220 are configured in an asymmetrical pattern relative to the longitudinal axis L-L of the electrode paddle 1700.

As described in the following paragraphs, embodiments of the present invention also include electrode paddles having a plurality of contacts, wherein the contacts are configured on a plurality of paddle sections, and wherein the contacts within each paddle section are arranged in a non-linear orientation. Embodiments of the present invention also include electrode paddles having a plurality of paddle sections wherein at least one of the paddle sections includes a plurality of contacts arranged in a non-linear pattern, and wherein one of the paddle sections may not include a plurality of contacts, or where the contacts are located in a linear arrangement. The various possible configurations noted above offer advantages for placement and stimulation of nerves/neural structures, particularly neural structures located at certain areas of the spine.

Referring now to FIG. 18A, and in accordance with embodiments of the present invention, an electrode paddle 1800 is shown, the electrode paddle 1800 having two paddle sections 1804a and 1804b. Various ways of interconnecting the paddle sections 1804a and 1804b are encompassed by the present invention. For the electrode paddle 1800 shown in FIG. 18A, two webbing bridges 1806 join the paddle sections 1804a and 1804b. Both paddle sections 1804a or 1804b include a plurality of contacts 220, where the contacts 220 are arranged in a non-linear pattern. Electrode paddle 1800 includes eight contacts, wherein four contacts are positioned on each paddle section 1804a and 1804b.

For the electrode paddle 1800, paddle sections 1804a and 1804b each include three contacts 220a, 220b and 220c aligned in a linear orientation, with a fourth contact 220d located off the axis of contacts 220a-c. More particularly, the contacts 220a-c are oriented co-axially and in a direction substantially parallel with the longitudinal axis L-L of the electrode paddle 1800, and contact 220d is located substantially adjacent an end contact of the co-axially oriented contacts 220a-c, such as adjacent contact 220c.

The contacts 220a-d are preferably individually and separately controllable using an implantable pulse generator. In addition, the contacts may also be controlled in groups of more than one. By way of example and not limitation, the contacts that are co-axially aligned and substantially parallel with the longitudinal axis L-L, that is, contacts 220a-c in FIG. 18A, are preferably separately controllable from contacts 220d. Furthermore, contacts 220c-d are also separately controllable from contacts 220a-b. As will be discussed and illustrated in more detail below, the non-linear arrangement of contacts 220a-d allows the electrode paddle sections 1804*a-b* to be implanted for stimulation of different neural structures to address pain at different areas of the patient's body.

For electrode paddle 1800, lead connections 1808*a* and 1808*b* preferably enter each paddle section 1804*a-b*, respectively, from an orientation that is transverse to the dorsal surface 1812 of the paddle section 1804*a-b*, such as in an orientation that is substantially perpendicular to the dorsal surface 1812. However, as with all electrode paddles described herein, it is to be understood that the electrode lead could also enter at an orientation that is substantially coplanar with the electrode paddle, such as at a longitudinal end of the paddle 1800, and such embodiments are also encompassed by the present invention.

The electrode paddle 1800 typically has a width 1816 between about 10 to 15 mm wide, and more preferably, about 13 mm wide, with a length 1820 of between about 15 to 25 mm long, and more preferably, about 20 mm long. For electrode paddle 1800, each paddle section 1804*a-b* is substantially L shaped as viewed from either a top or bottom plan view of the paddle sections 1800*a-b*.

Referring now to electrode paddle 1800' of FIG. B, a modified version of the electrode paddle 1800 is shown, wherein electrode paddle 1800' includes paddle sections 1804*a'* and 1804*b'*, with contacts 220*a-d* configured similar to those for electrode paddle 1800 discussed above. However, paddle sections 1804*a'* and 1804*b'* include a diagonally oriented interior edge portion 1824, in contrast to a longitudinally oriented interior edge portion 1828 and laterally oriented interior edge portion 1832 of electrode paddle 1800. Alternatively, the area between paddle sections 1804*a* and 1804*b* of electrode paddle 1800, and between paddle sections 1804*a'* and 1804*b'* of electrode paddle 1800', may be a continuous webbing 308, with or without a groove 310, perforations 312, or score 314. For the electrode paddle 1800' shown in FIG. 18B, two webbing bridges 1806 join the paddle sections 1804*a'* and 1804*b'*. As with electrode paddle 1800, electrode paddle 1800' includes lead connections 1808*a'* and 1808*b'* that preferably enter each paddle section 1804*a'-b'*, respectively, from an orientation that is transverse to the dorsal surface 1812 of the paddle section 1804*a'-b'*, such as in an orientation that is substantially perpendicular to the dorsal surface 1812. Electrode paddle 1800' preferably comprises dimensions similar to those described for electrode paddle 1800.

Referring now to FIG. 19A, electrode paddle 1800 is shown wherein interior paddle section connectors 1900 are located along the longitudinally oriented interior edge portion 1828 and the laterally oriented interior edge portion 1832. The interior paddle section connectors 1900 allow the surgeon or his or her staff to cut and trim the interior paddle section connectors 1900 before or during surgery to accommodate the patient's neuron-stimulation needs. FIG. 19A further illustrates an arrangement of flanges, wherein longitudinal flanges 1904 are located on the longitudinal ends 1908 of the electrode paddle 1800, and lateral flanges 1912 are located on the lateral sides 1916 of the electrode paddle 1800. As discussed previously, the flanges provide structure connected to the electrode paddle 1800 that is spaced apart from the contacts 220 and can be positioned under the lamina of one or more vertebra for holding and maintaining the position of the electrode paddle 1800 or its sections 1804*a-b*. The longitudinal flanges 1904 and lateral flanges 1912 may be a specific size, or alternatively, the longitudinal flanges 1904 and lateral flanges 1912 may be oversized to allow the surgeon or the surgeon's staff to trim them to accommodate the patient's physiological needs. As those skilled in the art will appreciate, the longitudinal flanges 1904 and lateral flanges 1912 can also be removed from the electrode paddle 1800 or its paddle sections 1804*a* and 1804*b*, such as by cutting the flanges during or prior to surgery. The longitudinal flanges 1904 and lateral flanges 1912 shown in FIG. 19A also apply to other electrode paddles as described herein, such as electrodes paddles 212 and 1800'.

Figure 19B:
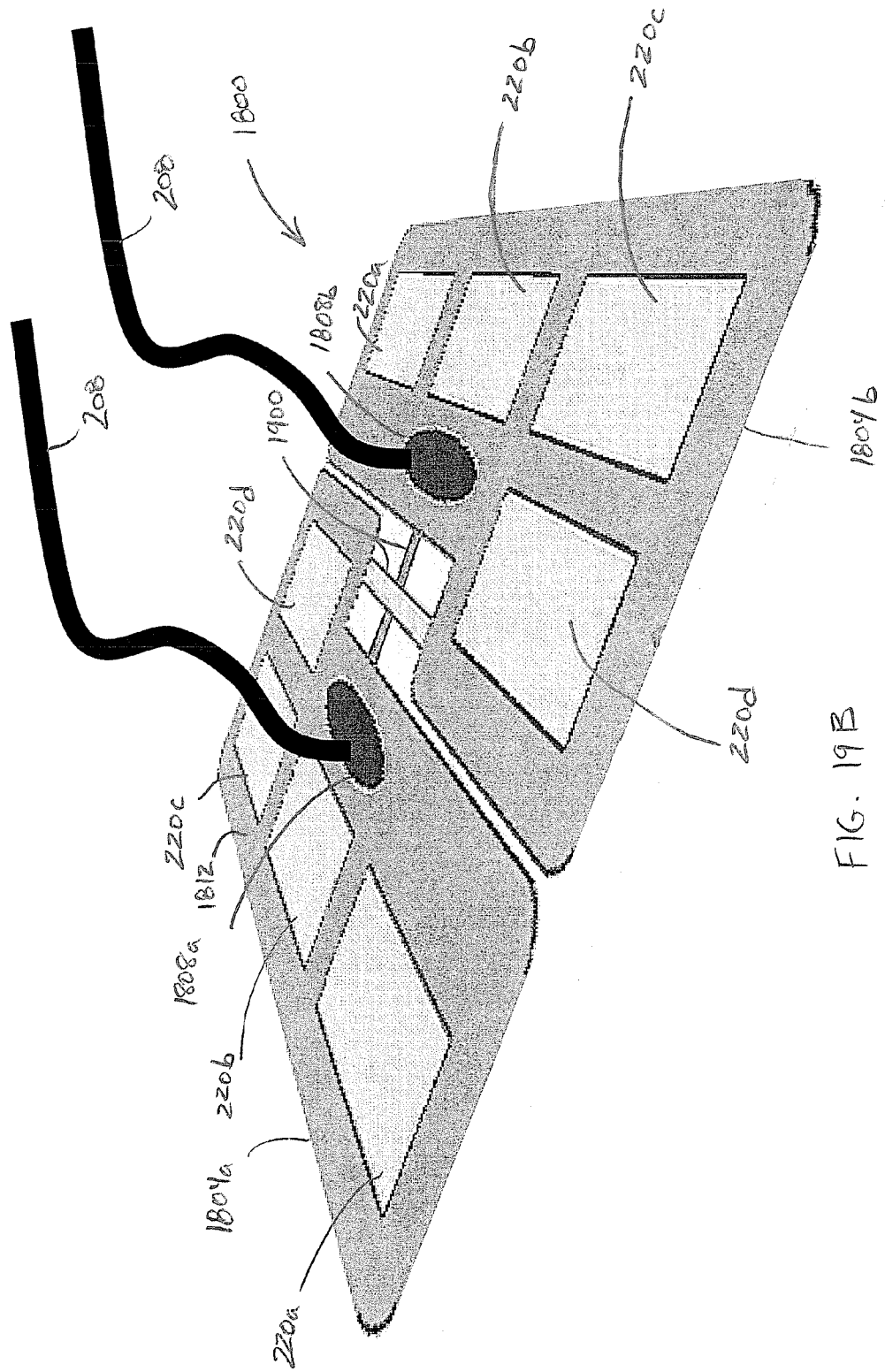

Referring now to FIGS. 19B and 19C, perspective views of the electrode paddle 1800 of FIG. 19A are shown, wherein the electrode paddle 1800 does not include longitudinal flanges 1904 and lateral flanges 1912. Leads 208 for controlling the contacts 220*a-d* on each paddle section 1804*a-b* are shown, wherein the leads 208 carry the electrical current from the implantable pulse generator (not shown in FIGS. 19B-C) to the contacts 220*a-d* by way of the lead connections 1808*a* and 1808*b*.

Referring now to FIG. 20, electrode paddle 1800 is shown having a pair of exterior paddle section connectors 2000 with one exterior paddle section connector 2000 located at each longitudinal end 1908 of the electrode paddle 1800. The exterior paddle section connectors 2000 interconnect the paddle sections 1804*a* and 1804*b*, and may be cut and trimmed to separate the two paddle sections 1804*a* and 1804*b*. The exterior paddle section connectors 2000 shown in FIG. 20 also apply to other electrode paddles as described herein, such as electrodes paddles 212 and 1800'.

Referring now to FIGS. 21A-21C, an electrode paddle 1800 is shown FIG. 21A having a plurality of flanges, including lateral flanges 1912 and bridging longitudinal flanges 2100 at the longitudinal ends 1908 of the electrode paddle 1800. FIGS. 21B and 21C illustrate electrode paddle 1800' having a plurality of flanges, including lateral flanges 1912 and bridging longitudinal flanges 2100 at the longitudinal ends 1908 of the electrode paddle 1800'. The bridging longitudinal flanges 2100 extend along the longitudinal ends of both paddle sections 1804*a* and 1804*b* (or paddle sections 1804*a'* and 1804*b'* in the case of electrode paddle 1800'), and interconnect paddle sections 1804*a* and 1804*b* (or paddle sections 1804*a'* and 1804*b'* in the case of electrode paddle 1800'). Accordingly, to divide the electrode paddle 1800 of FIG. 21A into separate paddle sections 1804*a* and 1804*b*, the surgeon or his or her staff can cut the bridging longitudinal flanges 2100 along a lateral orientation, such as at lateral cut line 2104, thereby removing the bridging longitudinal flanges 2100 from the paddle sections 1804*a* and 1804*b*, or the bridging longitudinal flanges 2100 can be cut along longitudinal cut line 2108 to maintain flange portions 2100*a* and 2100*b* of the bridging longitudinal flanges 2100 along the longitudinal ends of the paddle sections 1804*a* and 1804*b*. As those skilled in the art will appreciate, one or more of the lateral flanges 1912 and bridging longitudinal flanges 2100 can be removed from the electrode paddle 1800 or its paddle sections 1804*a* and 1804*b*, such as by cutting the flanges during or prior to surgery. For example, lateral flanges 1912 can be removed by cutting the lateral flange 1912 at cut line 2112. As those skilled in the art will appreciate, electrode paddle 1800' of FIGS. 21B and 21C may be modified similarly. Bridging longitudinal flanges 2100 may be used with other electrode paddles described herein, such as electrode paddles 212 and 2200 (discussed below).

Figure 22:
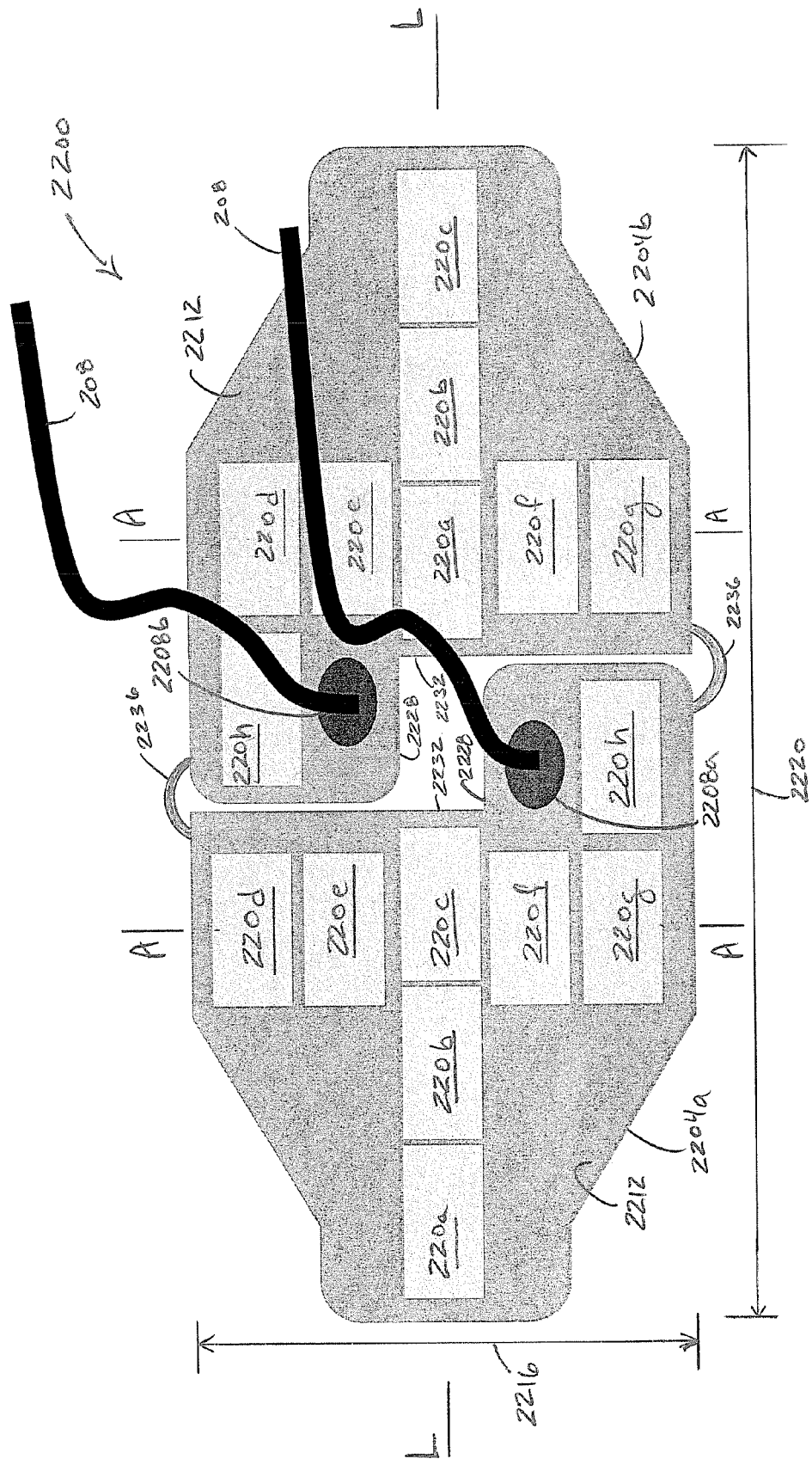
FIG. 22 is plan view of an electrode paddle in accordance with at least one embodiment of the present invention.

Referring now to FIG. 22, an electrode paddle 2200 in accordance with embodiments of the present invention is shown. The electrode paddle 2200 includes two paddle sections 2204*a* and 2204*b*. Both paddle sections 2204*a* and 2204*b* include a plurality of contacts 220, where the contacts 220 are arranged in a non-linear pattern. Electrode paddle 2200 includes sixteen contacts, wherein eight contacts are positioned on each paddle section 2204*a* and 2204*b*.

For the electrode paddle 2200 shown in FIG. 22, paddle sections 2204a and 2204b each include three contacts 220a, 220b and 220c aligned in a linear orientation substantially along the longitudinal axis L-L of the electrode paddle 2200. The electrode paddle sections 2204a and 2204b also include four additional contacts 220d, 220e, 220f, and 220g aligned along an axis transverse to the longitudinal axis L-L, and more preferably, aligned along an axis A-A substantially perpendicular to the longitudinal axis L-L. The contacts 220d-g may also be aligned with one of the contacts 220a-c; however, for the exemplary contacts configuration shown in FIG. 22, none of the contacts 220a-c are aligned with contacts 220d-g. The paddle sections 2204a and 2204 further include eighth contacts 220h located off the longitudinal axis L-L of contacts 220a-c and spaced apart from the transverse axis along which contacts 220d-g are located. More particularly, contact 220h is preferably located substantially adjacent and longitudinally aligned with an end contact of the co-axially oriented contacts 220d-g, such as contact 220g as seen in paddle section 2200a, or contact 220d as seen in paddle section 2204b. It will be appreciated by those skilled in the art that alternative contacts configurations to those described above are possible, and such configurations are within the scope of the present invention.

The contacts 220a-h are preferably individually and separately controllable using the implantable pulse generator. In addition, the contacts may also be controlled in groups of more than one. By way of example and not limitation, the contacts that are co-axially aligned and substantially parallel to or co-located with the longitudinal axis L-L, that is, contacts 220a-c in FIG. 22, are preferably separately controllable from contacts 220d-g. Furthermore, contacts 220g-h are also separately controllable from contacts 220a-c. As will be discussed and illustrated in more detail below, the non-linear arrangement of contacts 220a-h allows the electrode paddle sections 2204a-b to be implanted for stimulation of different neural structures to address pain at different areas of the patient's body.

Referring still to FIG. 22, for the electrode paddles 2204a and 2204b, lead connections 2208a and 2208b preferably enter each paddle section 2204a-b, respectively, from an orientation that is transverse to the dorsal surface 2212 of the paddle sections 2204a-b, such as in an orientation that is substantially perpendicular to the dorsal surface 2212. However, as with all electrode paddles described herein, it is to be understood that the electrode lead could also enter at an orientation that is substantially co-planar with the electrode paddle, such as at a longitudinal end of the paddle 2200, and such embodiments are encompassed by the present invention.

The electrode paddle 2200 typically has a width 2216 between about 15 to 25 mm wide, and more preferably, about 20 mm wide. In addition, the electrode paddle 2200 typically has a length 2220 of between about 35 to 55 mm long, and more preferably, about 45 mm long.

The area between the paddle sections 2204a and 2204b may comprise a continuous webbing, with or without a groove 310, perforations 312, or score 314. In accordance with at least one embodiment of the present invention, the electrode paddle 2200 comprises a longitudinally oriented interior edge portion 2228 and a laterally oriented interior edge portion 2232. However, it will be appreciated by those skilled in the art that alternative orientations for the interior edges of the electrode paddle 2200 are possible, and such configurations are within the scope of the present invention. As shown in FIG. 22, the paddle sections 2204a and 2204b are interconnected by exterior paddle section connectors 2236.

Figure 23:
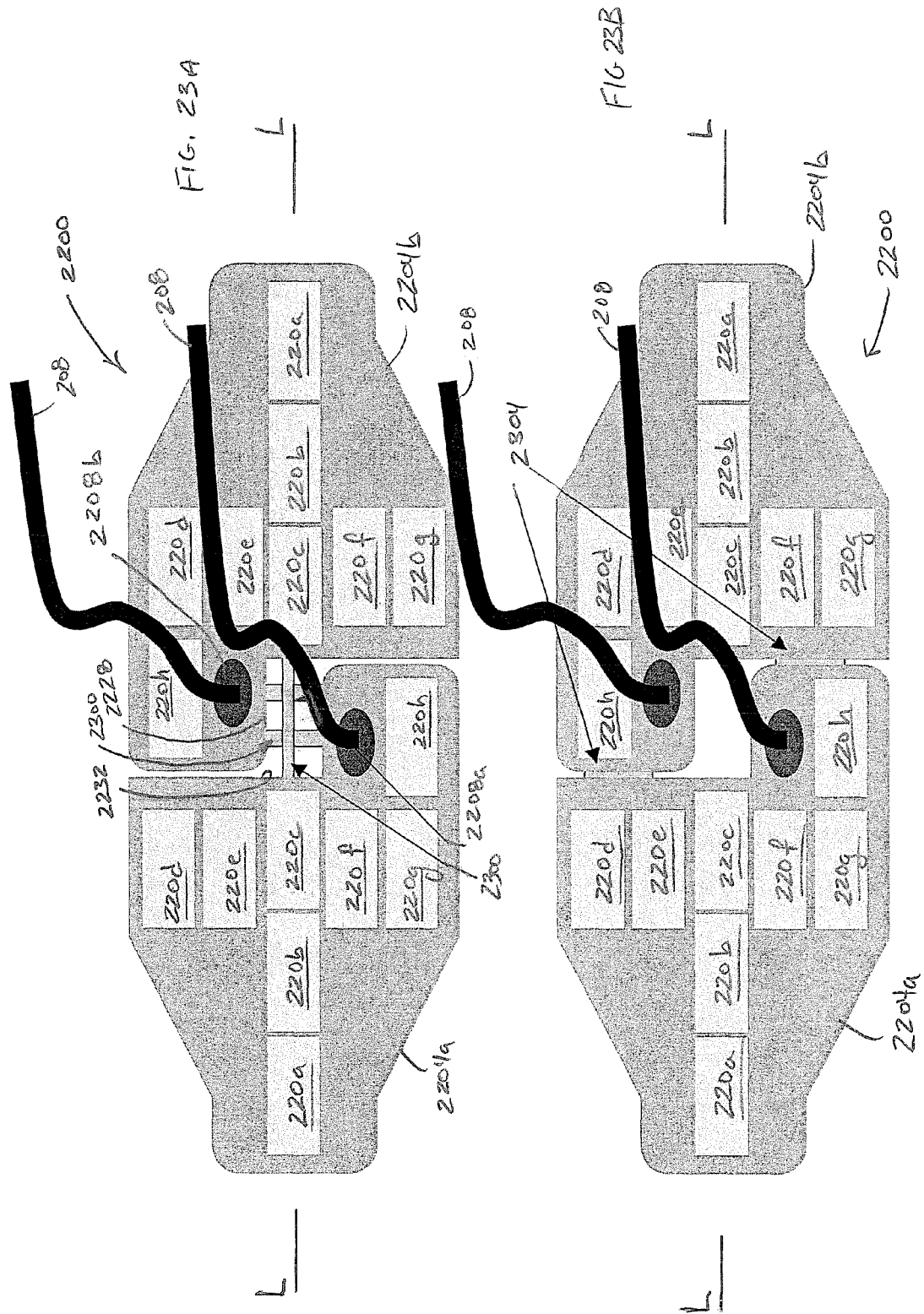
FIGS. 23A and 23B are plan views of electrode paddles in accordance with at least one embodiment of the present invention.

Referring now to FIG. 23A, and in accordance with at least one embodiment of the present invention, the paddle sections 2204a and 2204b of electrode paddle 2200 are interconnected by interior paddle section connectors 2300. The interior paddle section connectors 2300 are located along the longitudinally oriented interior edge portion 2228 and the laterally oriented interior edge portion 2232. For the electrode paddle 2200 shown in FIG. 23B, two webbing bridges 2304 join the paddle sections 2204a and 2204b.

Figure 24:
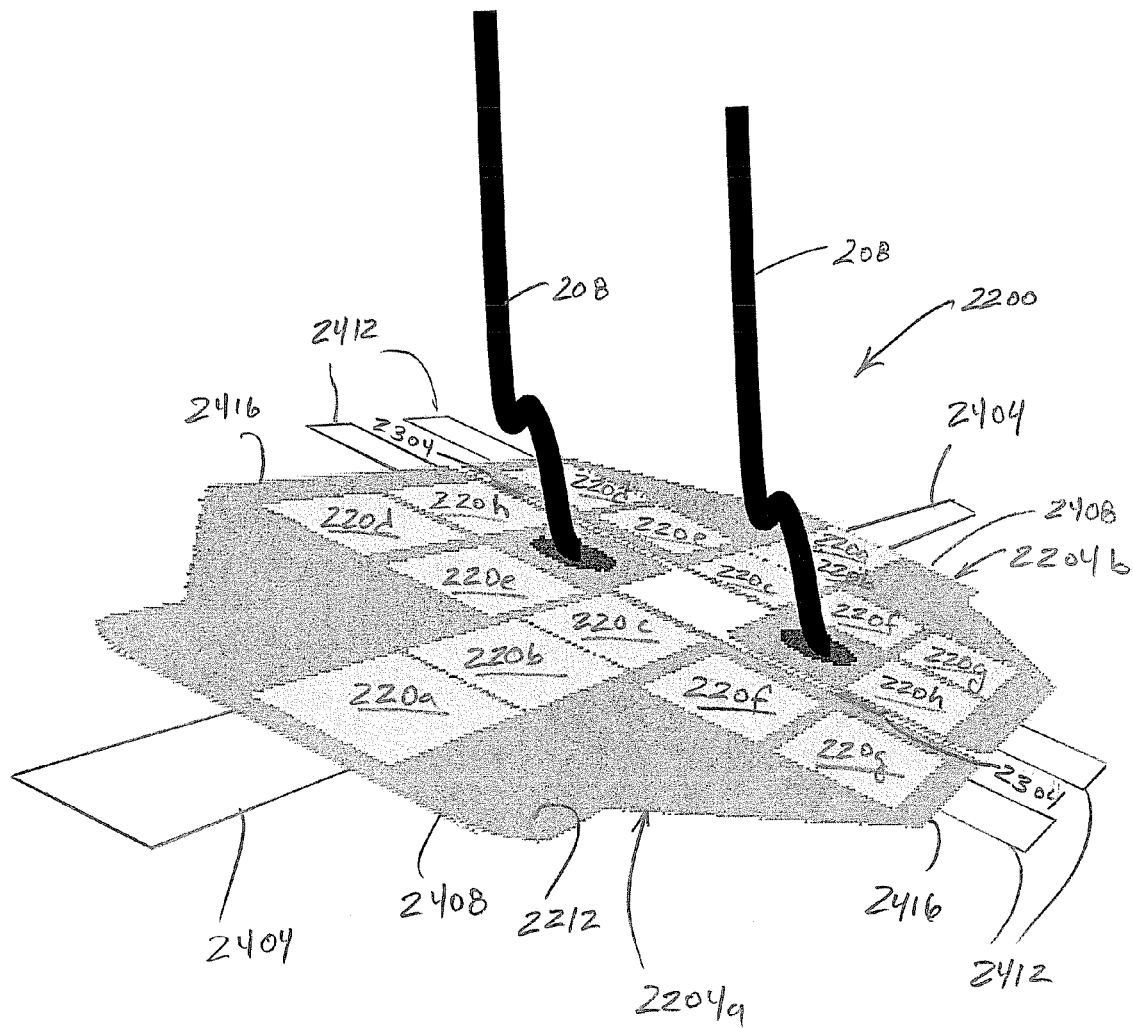
FIG. 24 is a perspective view of an electrode paddle in accordance with at least one embodiment of the present invention.

Referring now to FIG. 24, a perspective view of electrode paddle 2200 is shown. The paddle sections 2204a and 2204b of FIG. 24 each include a longitudinal flange 2404 located on the longitudinal ends 2408 of the electrode paddle 2200, and lateral flanges 2412 are located on the lateral sides 2416 of the electrode paddle 2200. As those skilled in the art will appreciate, the electrode 2200 may use bridging lateral flanges to interconnect the paddle sections 2204a and 2204b, wherein the flanges can be cut in a direction perpendicular to the longitudinal axis of the electrode paddle 2200 to separate the paddle sections 2204a and 2204b. Such a flange would be similar in structure to the bridging longitudinal flanges 2100 shown in FIG. 21A.

The longitudinal flanges 2404 and lateral flanges 2412 provide structure connected to the electrode paddle 2200 that is spaced apart from the contacts 220 and can be positioned under the lamina of one or more vertebra for holding and maintaining the position of the electrode paddle 2200 or its paddle sections 2204a-b. The longitudinal flanges 2404 and lateral flanges 2412 may be a specific size, or alternatively, the flanges longitudinal flanges 2404 and lateral flanges 2412 may be oversized to allow the surgeon or the surgeon's staff to trim them to accommodate the patient's physiological needs. The longitudinal flanges 2404 and lateral flanges 2412 can also be removed from the electrode paddle 2200 or its paddle sections 2204a and 2204b, such as by cutting the flanges during or prior to surgery.

Various embodiments of the present invention are particularly useful for treatment of neural structures accessible between the first cervical vertebra (C1) and second cervical vertebra (C2), between the seventh, eighth, ninth, tenth and eleventh thoracic vertebrae (T7-T11), and between the, fourth lumbar vertebra (L4), fifth lumbar vertebra (L5) and the sacrum (S). More particularly, because of the distribution of neural structures and the configuration of the above noted vertebrae, the placement of an electrode paddles in accordance with embodiments of the present invention can be particularly useful.

In order to facilitate placement of an electrode paddle in the vicinity of the target neural structures, a surgeon may perform a partial laminectomy to remove a portion of one or more vertebrae. The electrode paddle can then be positioned such that the electrodes are not pressed against the neural structures by the dorsal bony structures, but rather, the electrode paddles are held in place, for example, by one or more flanges that are inserted or tucked under the lamina of the vertebra to hold the electrode paddle in place. Several of the figures illustrate locations of partial laminectomies that may be performed; however, these examples are provided for illustrative purposes only, and are not intended to be limiting nor fully illustrative of all occasions when a partial laminectomy may be necessary or advantageous. It is further noted that the electrode paddles presented herein may be used to treat a variety of indications. Thus, the examples shown are not meant to be limiting nor are they the full possible range of orientations and uses of the electrode paddles described herein. Accordingly, although each electrode paddle described herein is not illustrated for use in every possible orientation at every possible anatomical treatment location, a number of examples are presented to illustrate possible uses of the electrode paddles of the present invention, and those skilled in the art will appreciate that other uses and/or orientations are readily possible.

Figure 25:
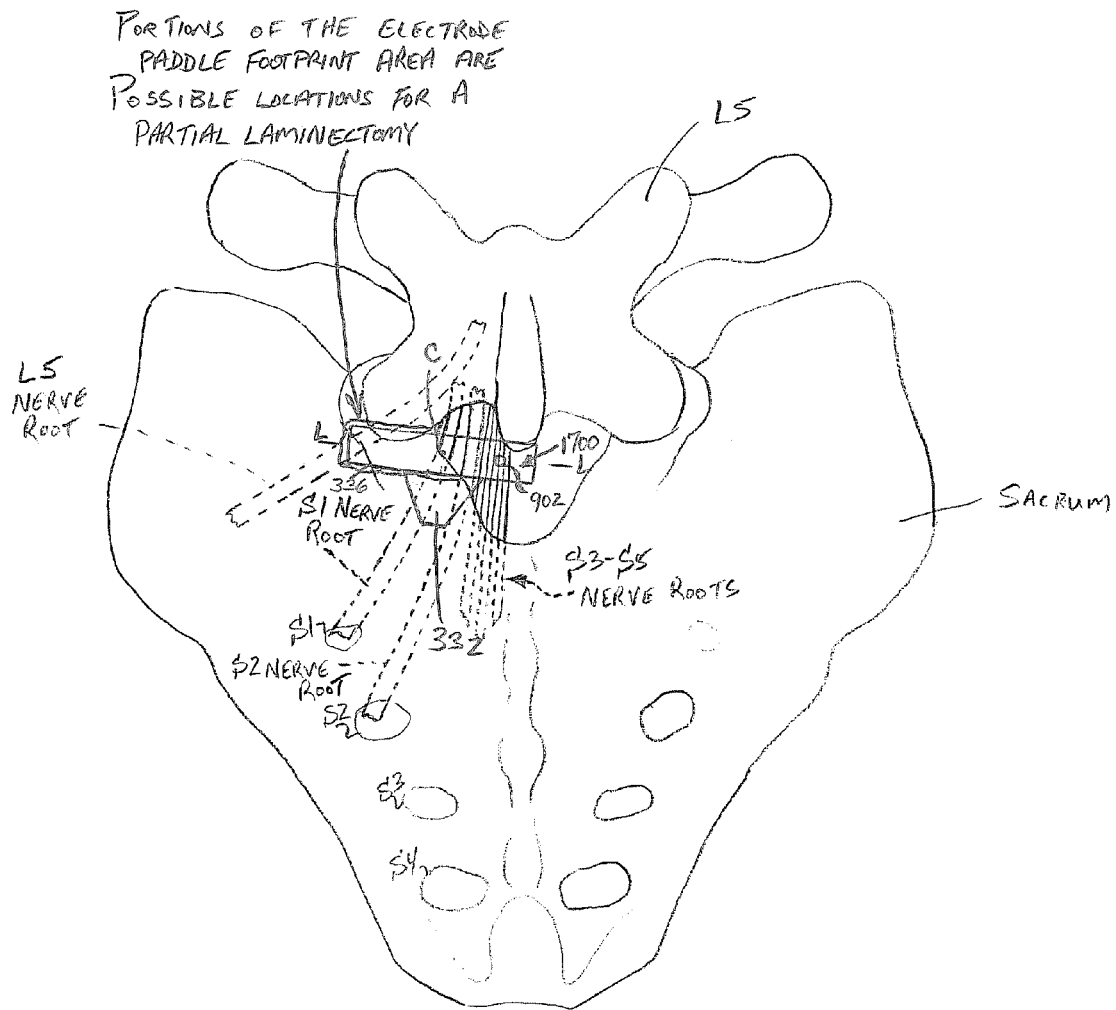
FIGS. 25-38 are posterior views of the L5-S vertebrae with exemplary uses of embodiments of the present invention.

Referring now to FIGS. 25-38, and by way of example and not limitation, several illustrative examples of the placement of the electrode paddles of the present invention between the L5-S1 vertebrae are shown. FIG. 25 illustrates the L5-S1 vertebrae with a single electrode paddle 1700 oriented with its longitudinal axis L-L aligned transverse to the orientation of the spine. The electrode paddle 1700 advantageously includes a lead connection 902 that is offset from longitudinal center C of the electrode paddle 1700. The electrode paddle 1700 also includes one flange 332 located along a lateral side 336 of the electrode paddle 1700. FIG. 25 further illustrates the location of a partial laminectomy, wherein some bone of the sacrum has been removed so that the electrodes of the electrode paddle 1700 are not pressed against the neural structures. However, the flange 332 is tucked under a portion of the sacrum to maintain the location of the electrode paddle 1700.

Figure 26:
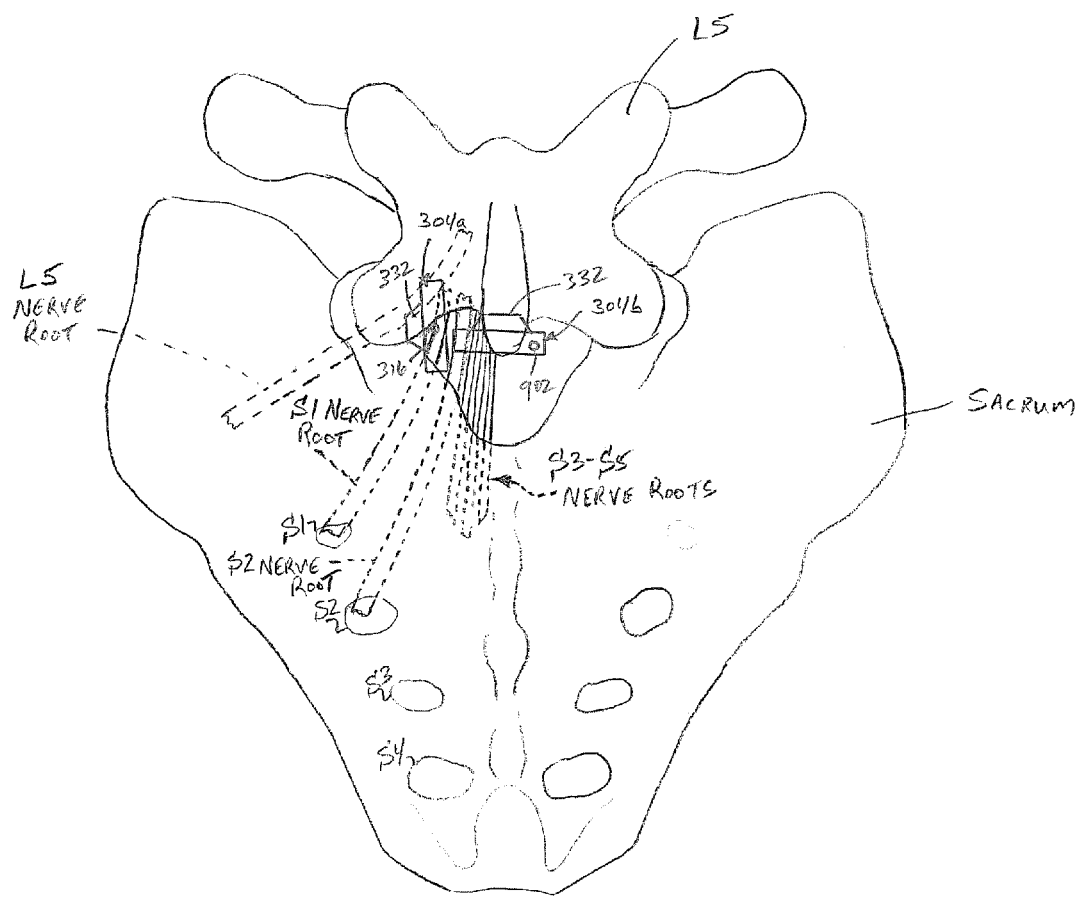

FIG. 26 illustrates the L5-S1 vertebrae with first and second paddle sections oriented transverse to each other. More particularly, paddle section 304a is oriented with its longitudinal axis L-L nearly parallel to the patient's spine, while detached paddle section 304b is aligned substantially perpendicular to the orientation of the spine. Paddle section 304a includes a lead connection 316 at substantially the longitudinal center of the paddle section 304a, while paddle section 304b includes a lead connection 902 offset from the longitudinal center of the paddle section 304b. The combination of the paddle sections 304a and 304b as shown in FIG. 26 allows a single implantable pulse generator 204 to provide electrical stimulation to two paddle sections, that is, paddle sections 304a and 304b, where the electrical signal is conveyed along a single electrode lead 208 that divides to provide the electrical signal to the paddle sections 304a and 304b.

Figure 27:
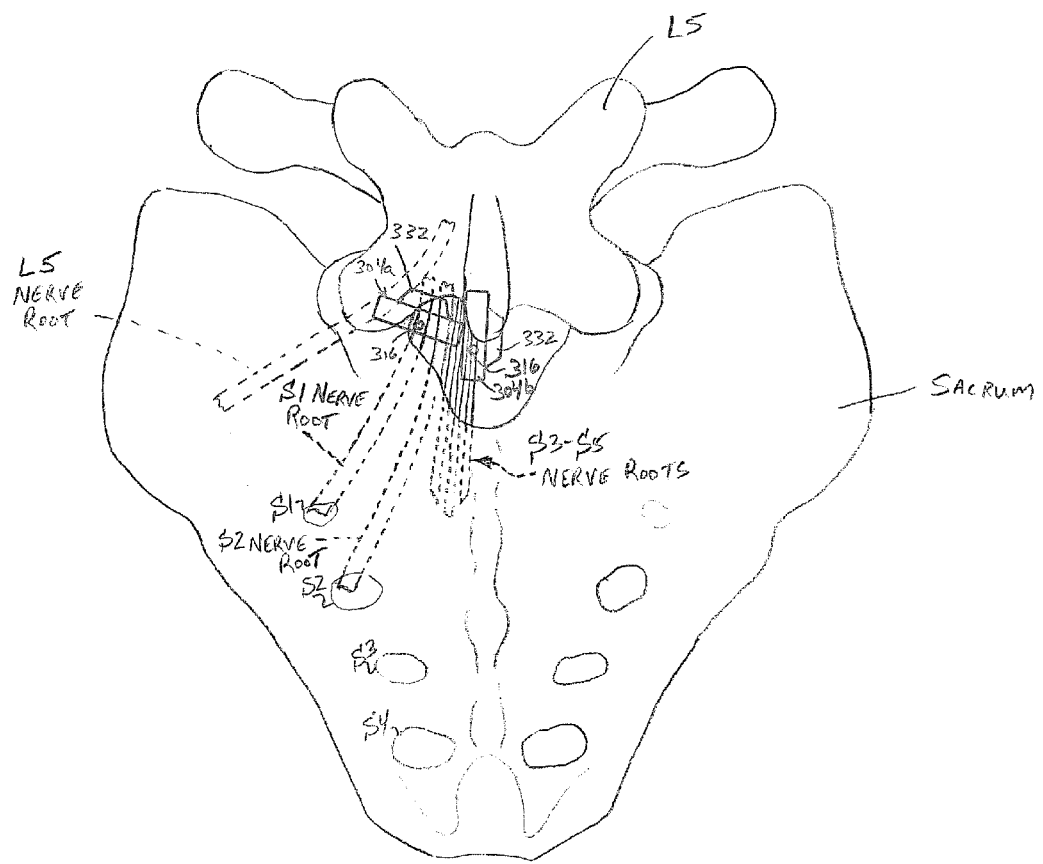

FIG. 27 illustrates the L5-S1 vertebrae with first and second paddle sections oriented transverse to each other. More particularly, paddle section 304a is oriented with its longitudinal axis L-L aligned transverse to the patient's spine, while detached paddle section 304b is aligned substantially parallel to the orientation of the spine. Upon comparing the orientation of the paddle sections 304a and 304b shown in FIGS. 26 and 27, it is apparent that the present invention provides the surgeon the ability to orient the paddle sections to stimulate the neural structures necessary to treat the patient as may be needed. For example, as shown in FIG. 26, paddle section 304a is aligned to stimulate the L5 and S1 nerve roots, while in FIG. 27 the paddle section 304a is aligned transverse to the L5 and S1 nerve roots to also allow stimulation of the S2 nerve root.

Figure 28:
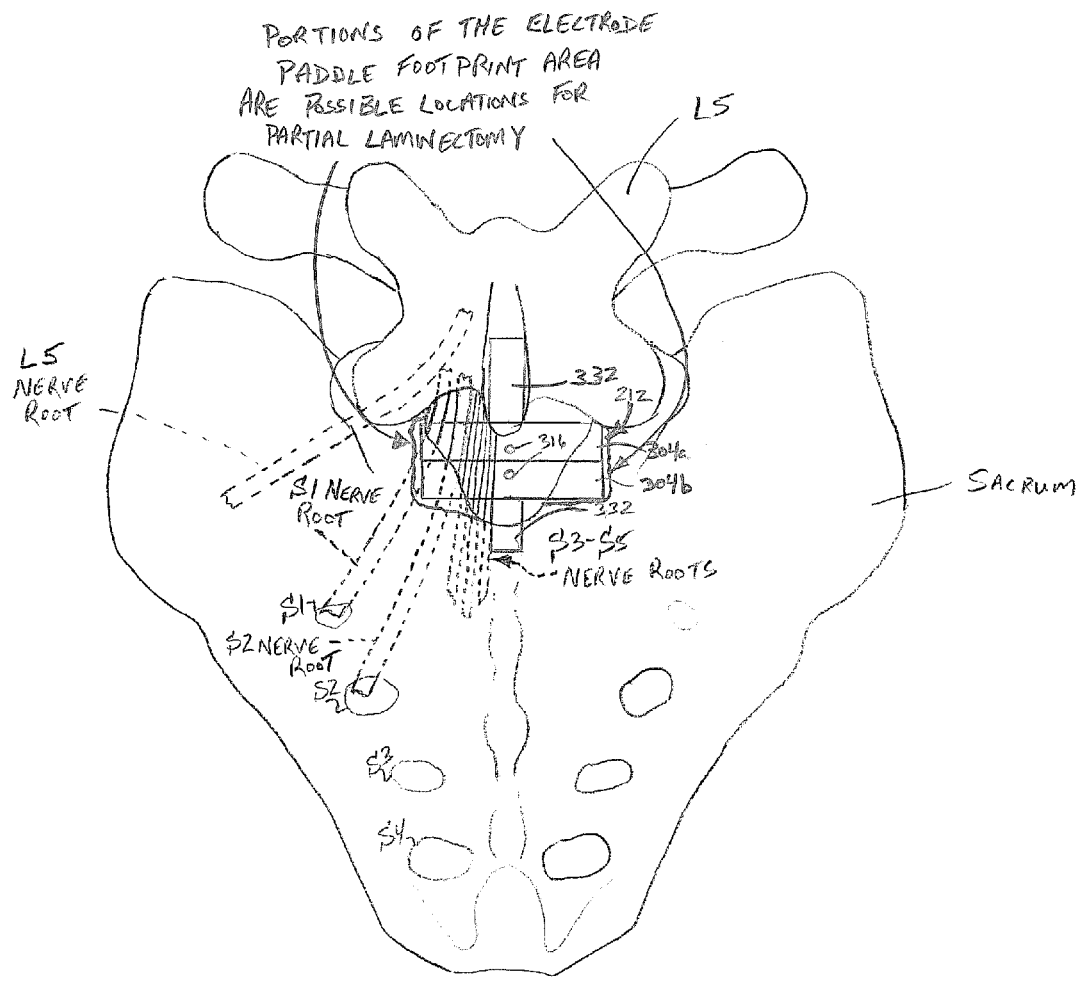

FIG. 28 illustrates the L5-S1 vertebrae with an electrode paddle 212, where the electrode paddle 212 is undivided so that paddle section 304a is connected to paddle section 304b. With flanges 332 and the dorsally positioned lead connections 316, the electrode paddle 212 can be positioned to stimulate the desired neural structures.

Figure 29:
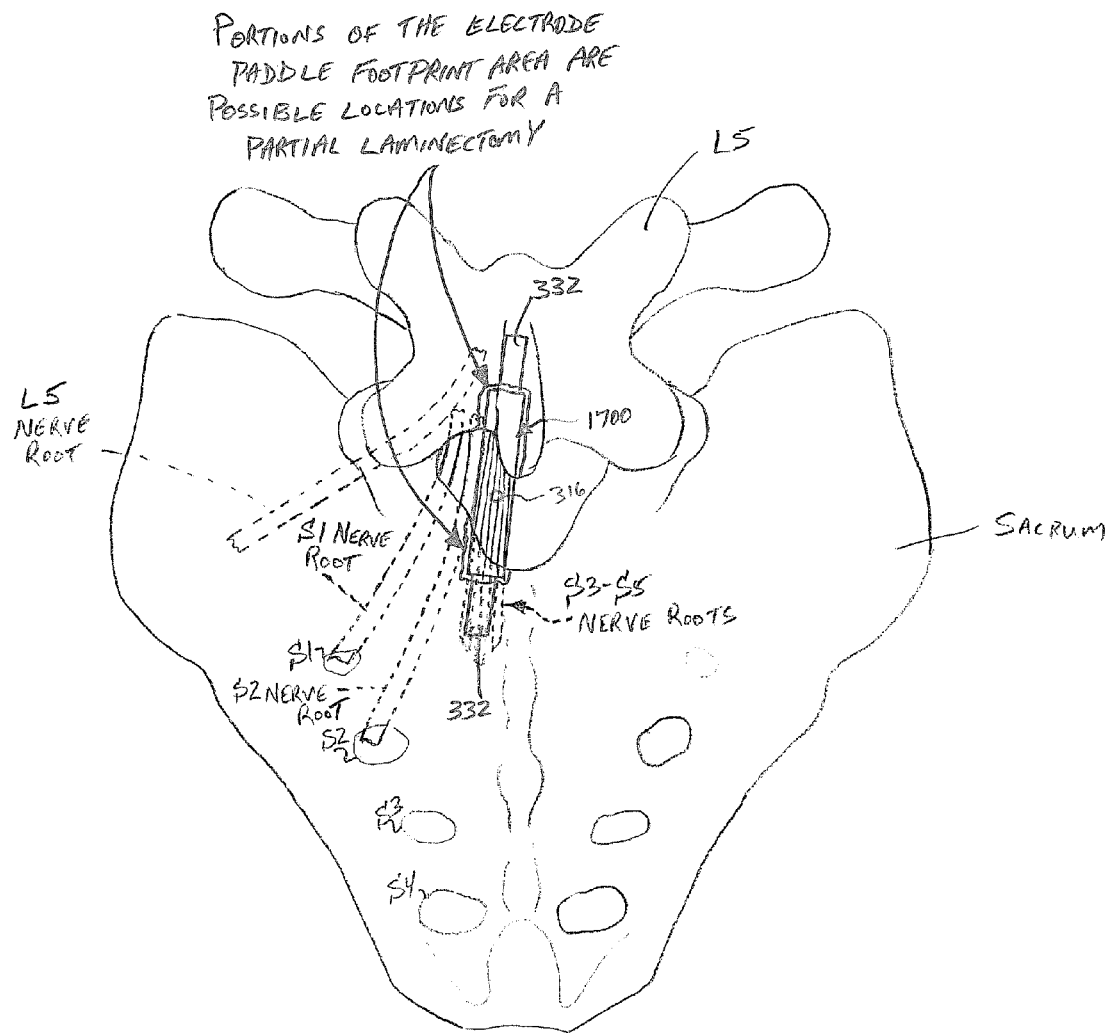

FIG. 29 illustrates the L5-S1 vertebrae with a single electrode paddle 1700 oriented with its longitudinal axis L-L aligned substantially parallel to the orientation of the S3-S5 nerve roots. For the electrode paddle 1700 shown in FIG. 29, the dorsally projecting lead connection 316 allows the electrode paddle to cover the targeted S3-S5 nerve roots.

Figure 30:
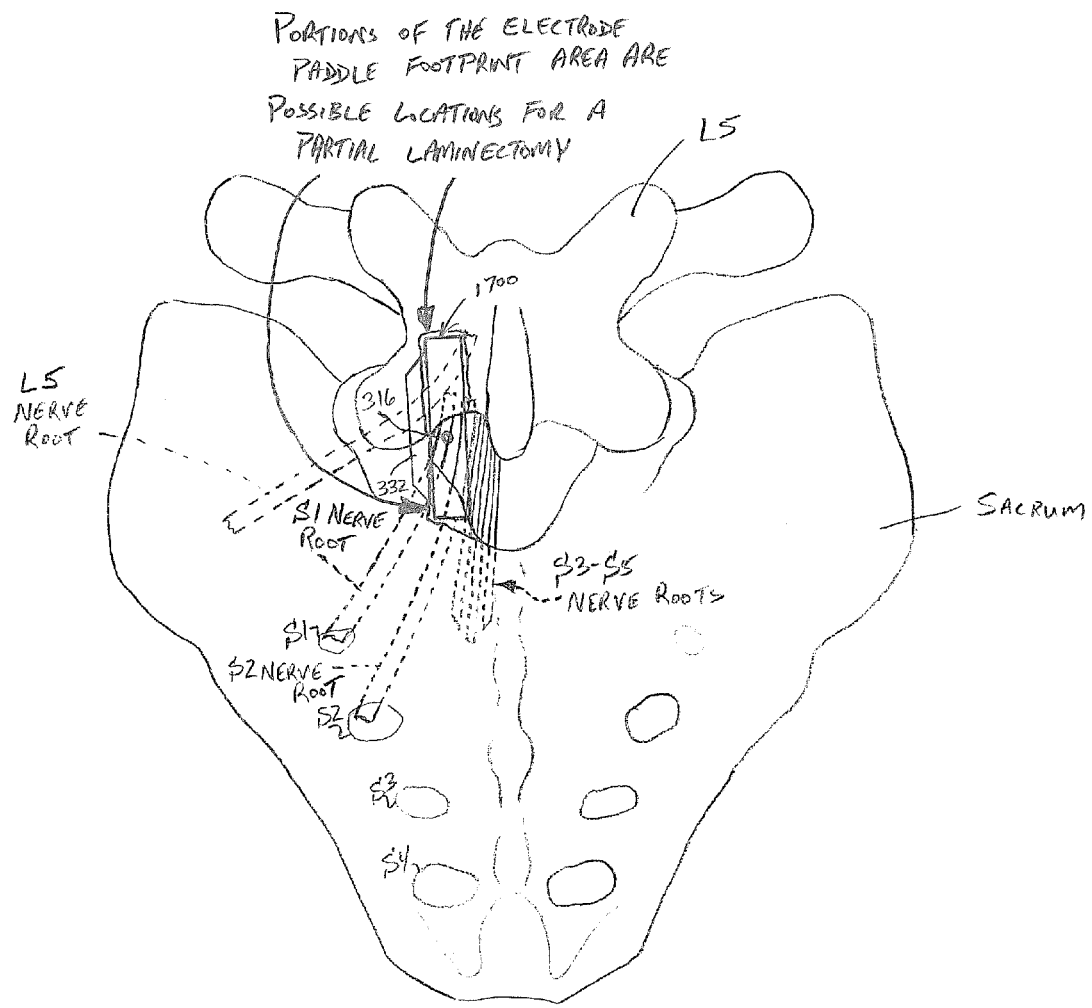

FIG. 30 illustrates the L5-S vertebrae with a single electrode paddle 1700 oriented with its longitudinal axis L-L aligned nearly parallel to the orientation of the spine to stimulate the L5, S1 and S2 nerve roots. For the electrode paddle 1700 shown in FIG. 30, the dorsally projecting lead connection 316 allows the electrode paddle to cover the targeted nerve roots.

Figure 31:
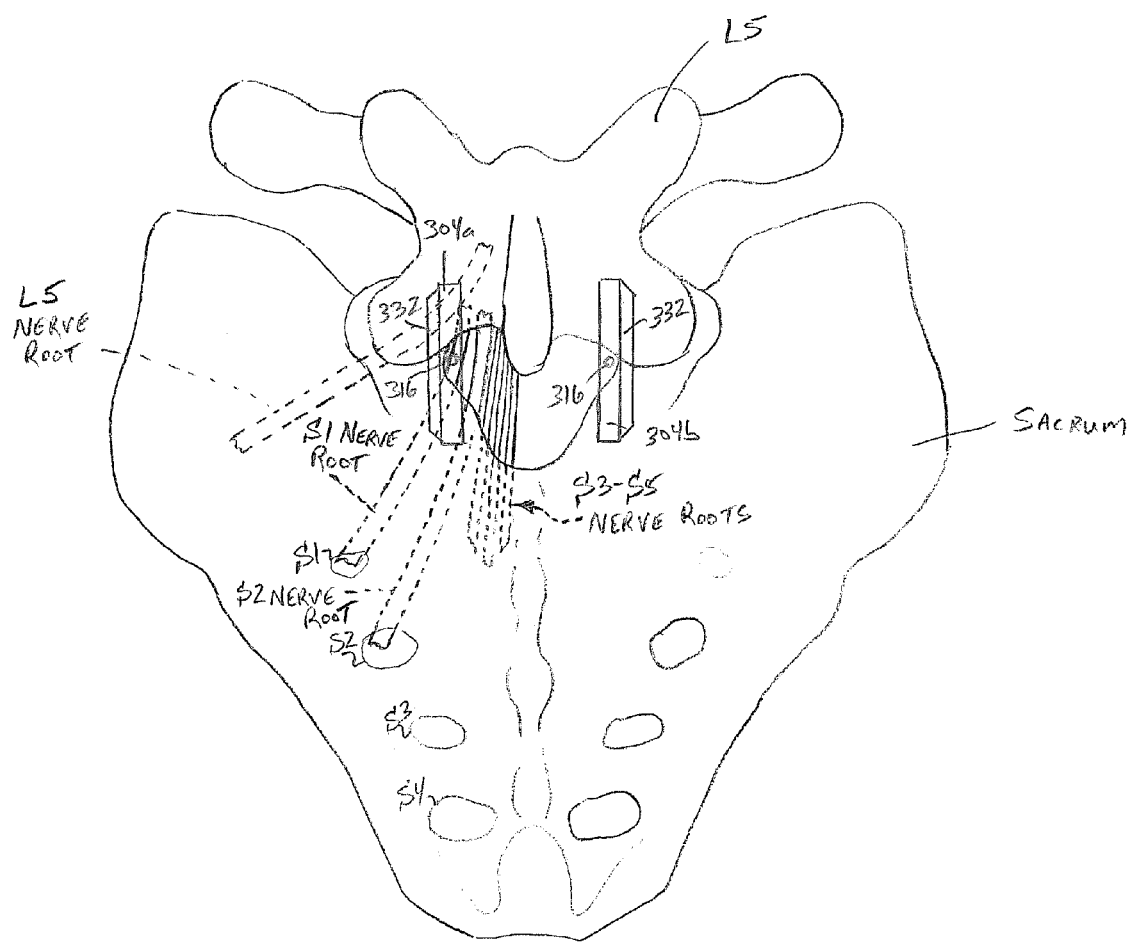

FIG. 31 illustrates the L5-S vertebrae with two paddle sections 304a and 304b. The two paddle sections 304a and 304b are positioned with one paddle section on each side of the spinous process, and with the paddle sections 304a and 304b oriented with their longitudinal axis L-L aligned nearly parallel to the orientation of the spine to bilaterally stimulate the L5 and S1 nerve roots. The dorsally projecting lead connection 316 allows the paddle sections 304a and 304b to cover the targeted nerve roots.

Figure 32:
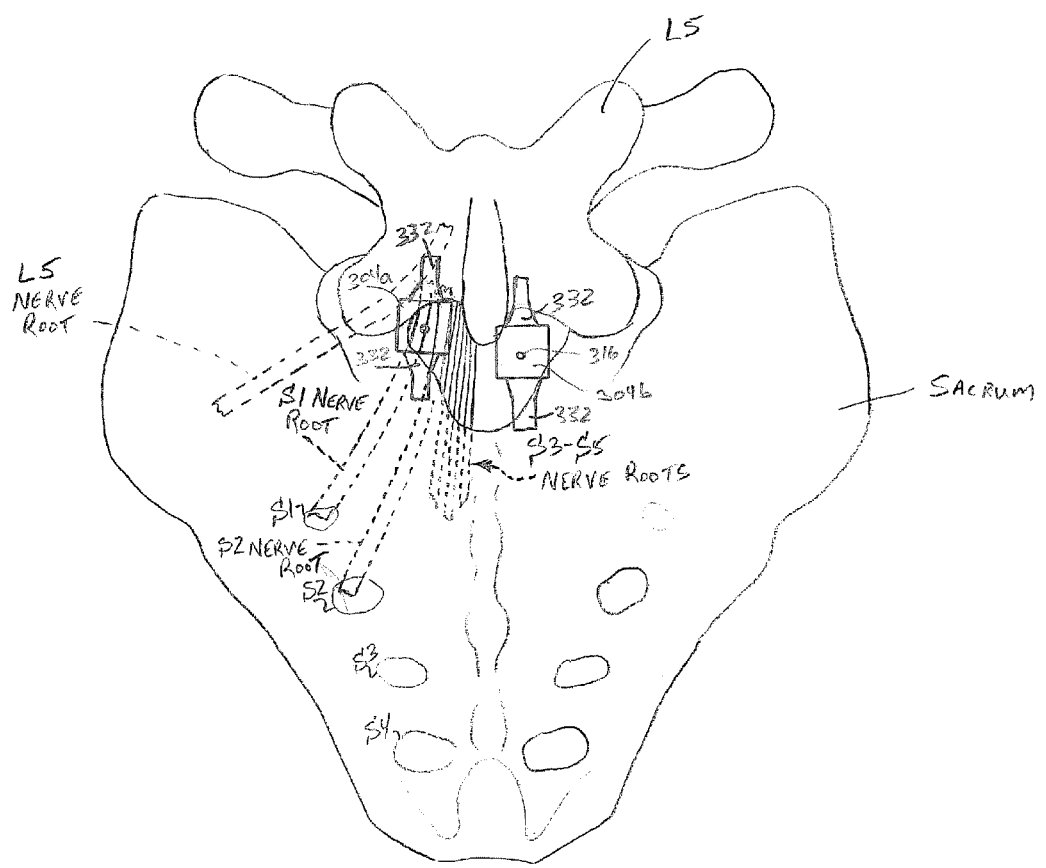

FIG. 32 illustrates the L5-S1 vertebrae with two paddle sections 304a and 304b, where the paddle sections 304a and 304b correspond to those shown in FIGS. 12 and 13. The two paddle sections 304a and 304b are positioned with one paddle section on each side of the spinous process. The flanges 332 are placed under the lamina to maintain the position of the paddle sections 304a and 304b. In addition, the dorsally projecting lead connections 316 allows the paddle sections 304a and 304b to cover the targeted nerve roots.

Figure 33:
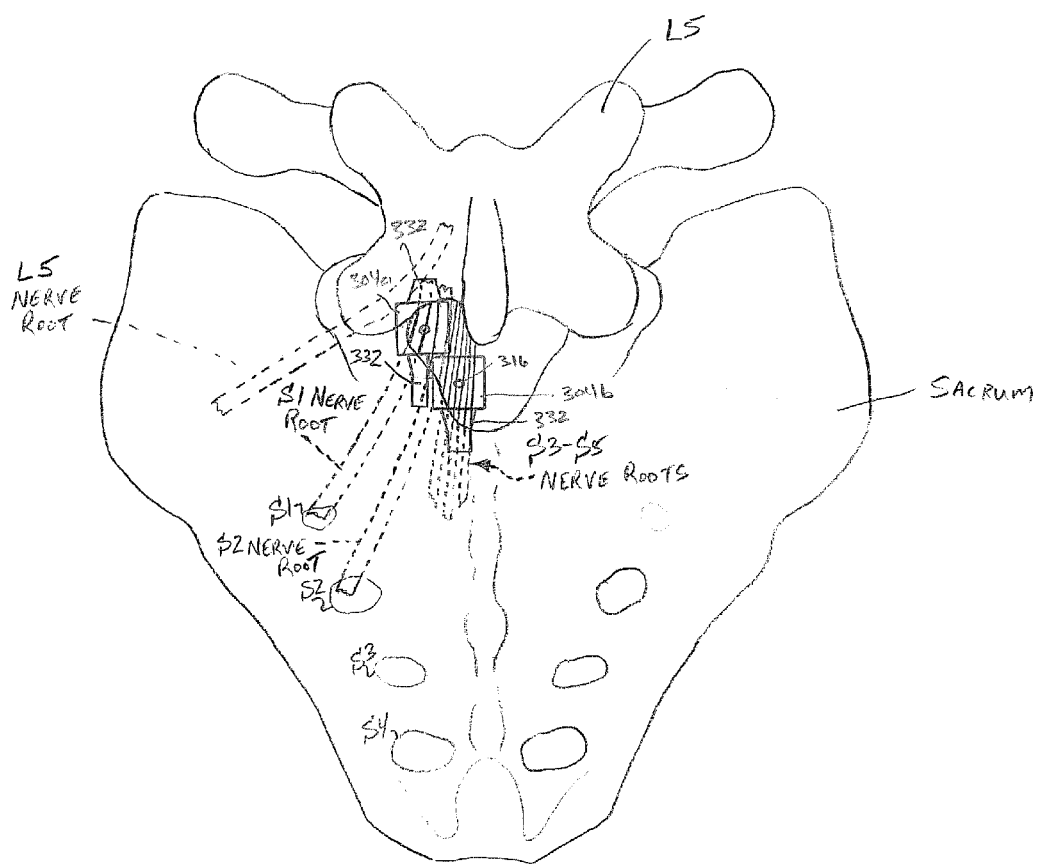

Referring now to FIG. 33, similar paddle sections 304a and 304b to those shown in FIG. 32 are depicted on a single side of the spinous process. In addition, the paddle sections 304a and 304b of FIG. 33 illustrate flanges 332 placed under the lamina to maintain the position of the paddle sections 304a and 304b. The dorsally projecting lead connections 316 allow the paddle sections 304a and 304b to cover the targeted nerve roots.

Figure 34:
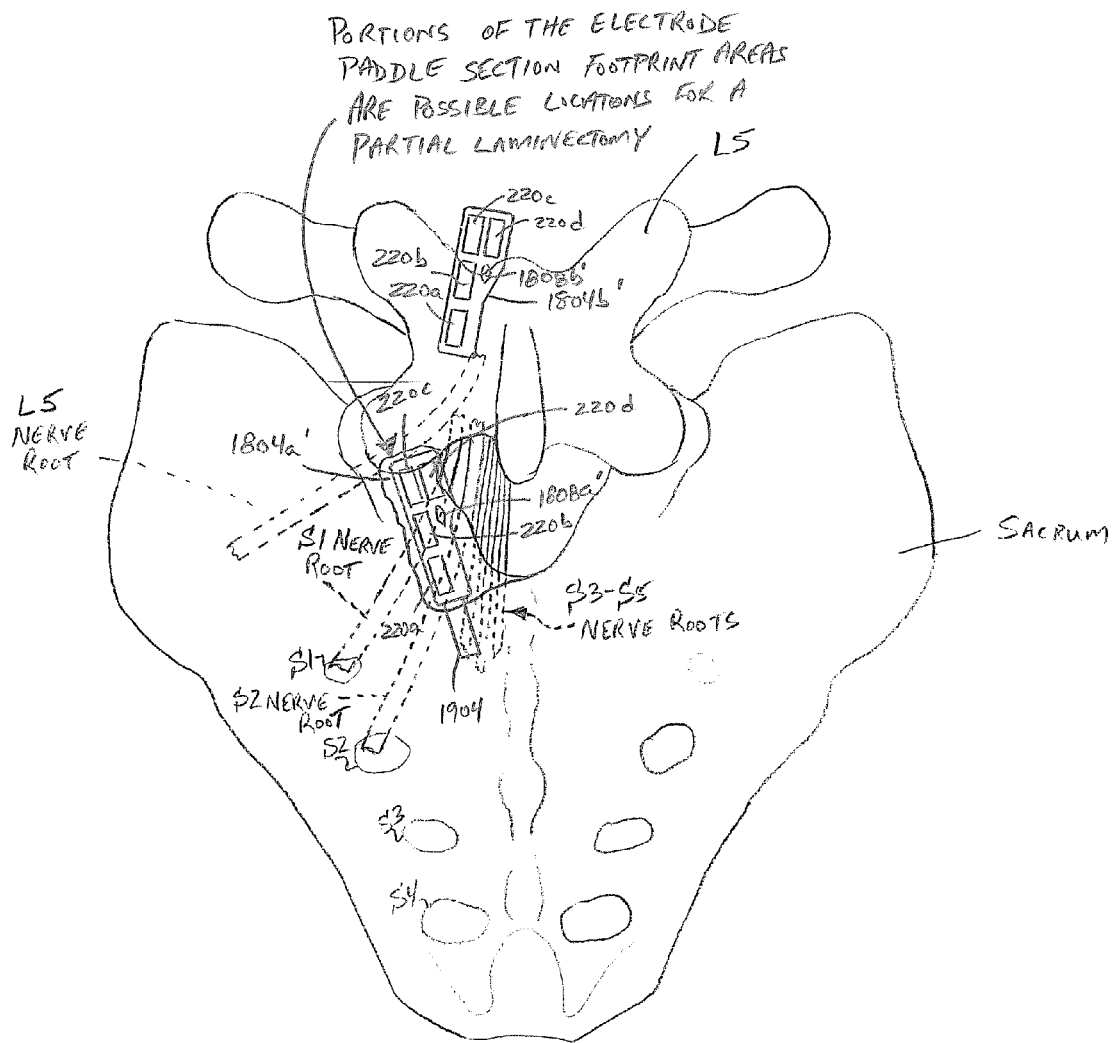

FIG. 34 illustrates the use of paddle sections 1804a' and 1804b' of electrode paddle 1800' where the paddle sections 1804a' and 1804b' have been separated from one another and are placed to stimulate the L4, L5, S1 and/or S2 nerve roots unilaterally. FIG. 34 further illustrates the location of a partial laminectomy, wherein some bone of the sacrum has been removed so that the contacts 220a-d of the paddle section 1804a' are not pressed against the neural structures. However, the flange 1904 is tucked under a portion of the sacrum to maintain the location of the paddle section 1804a'.

Figure 35:
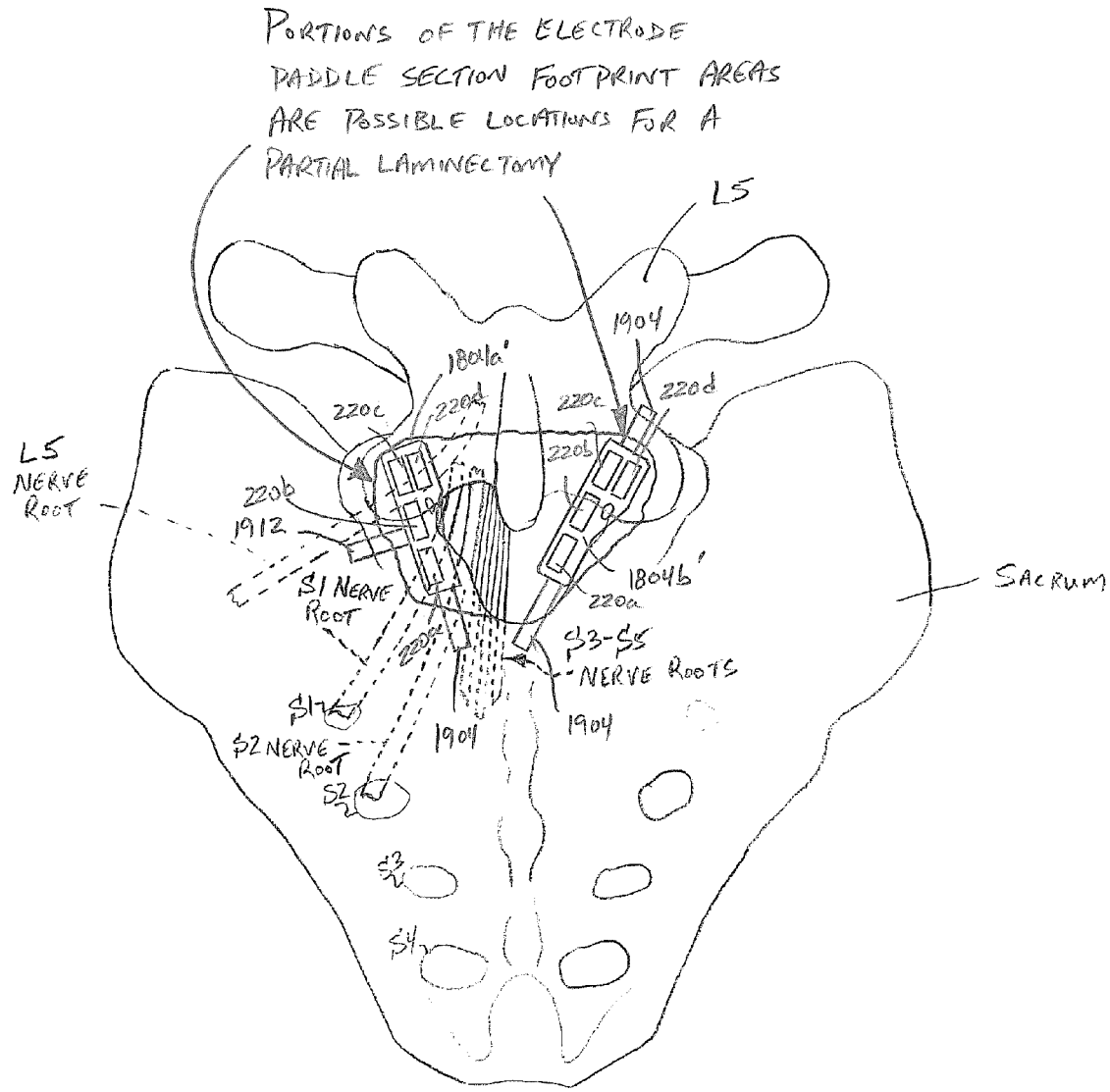

FIG. 35 illustrates the use of paddle sections 1804a' and 1804b' of electrode paddle 1800' where the paddle sections 1804a' and 1804b' have been separated from one another and are placed to stimulate the S1 and/or S2 nerve roots bilaterally. The flanges 1904 are tucked under a portion of the sacrum or lamina of the L5 vertebra to maintain the location of the paddle sections 1804a' and 1804b'.

Figure 36:
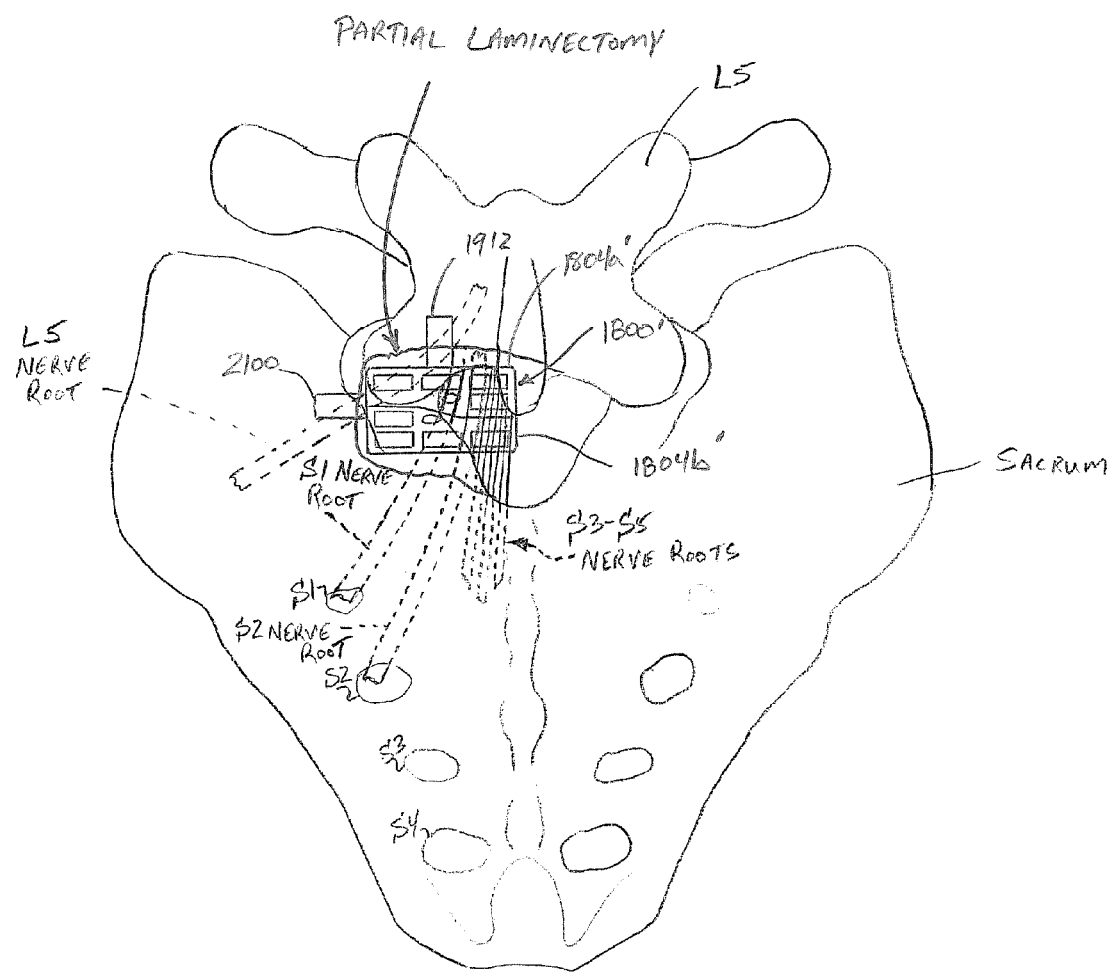

Referring now to FIG. 36, electrode paddle 1800' is shown with its paddle sections 1804a' and 1804b' still interconnected with the electrodes positioned to stimulate the S1, S2, and/or S3-5 nerve roots on the left side of the spine. Bridging longitudinal flange 2100 extends along the longitudinal end of both paddle sections 1804a' and 1804b' of electrode paddle 1800' and interconnects paddle sections paddle sections 1804a' and 1804b'.

Figure 37:
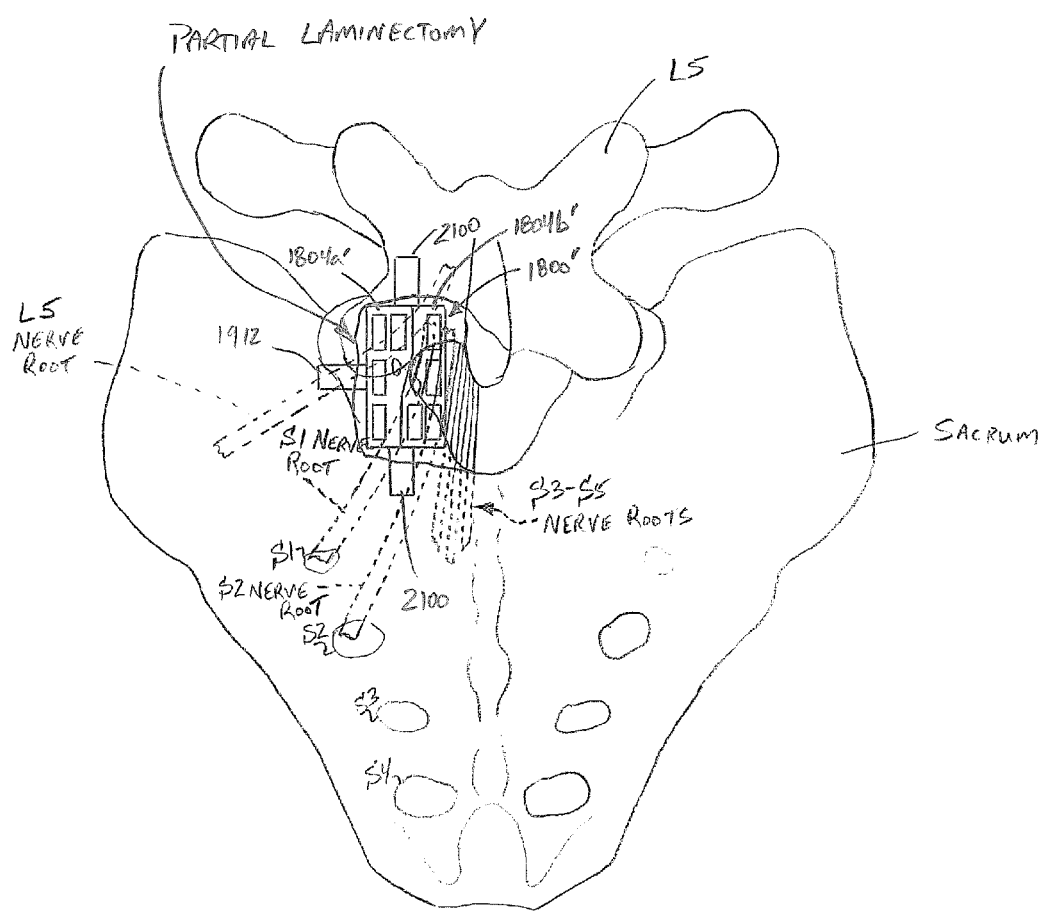

Referring now to FIG. 37, electrode paddle 1800' is shown with its paddle sections 1804a' and 1804b' still interconnected with the electrodes positioned to stimulate the L5, S1, and/or S2 nerve roots on the left side of the spine. The flanges 1912 and 2100 are tucked under a portion of the sacrum or lamina of the L5 vertebra to maintain the location of the electrode paddle 1800'.

Figure 38:
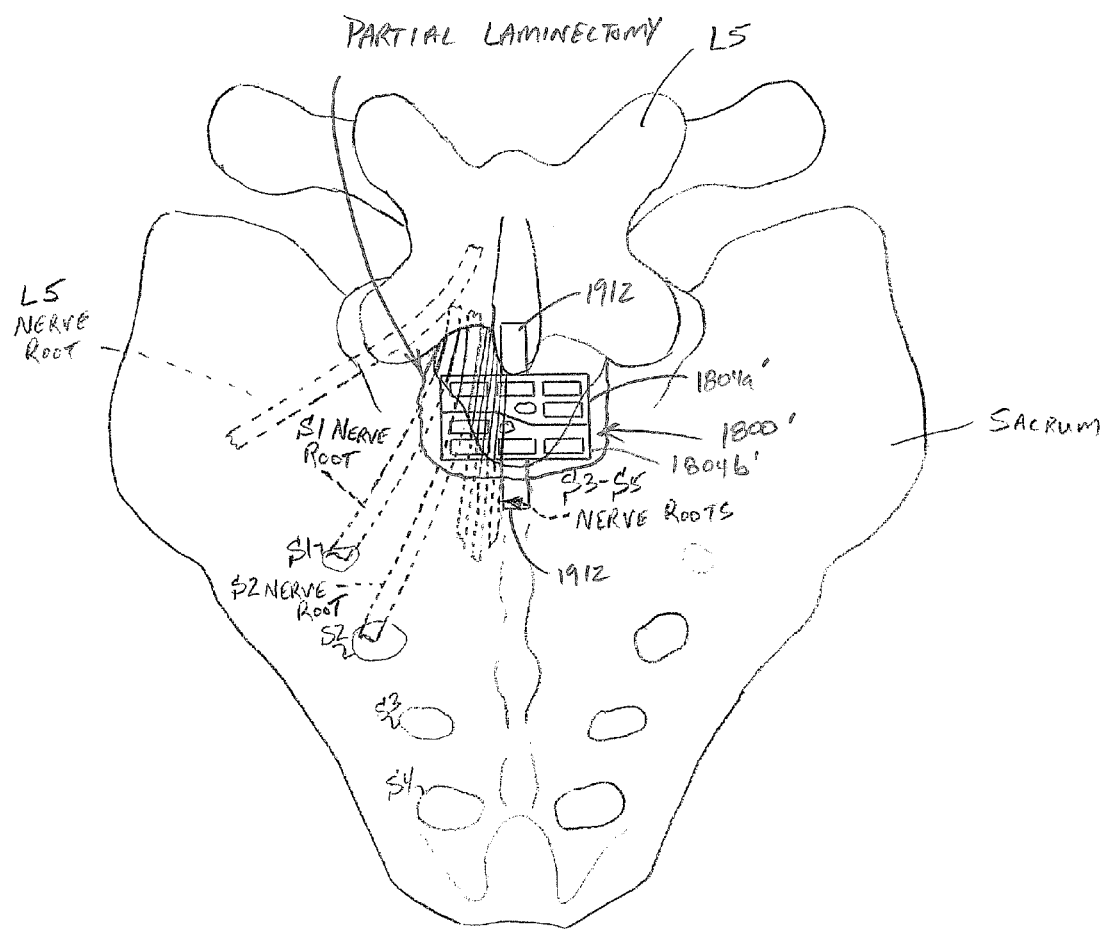

FIG. 38 illustrates another example of electrode paddle 1800' being used to with its paddle sections 1804a' and 1804b' still interconnected. For the example shown in FIG. 38, the electrodes are used to stimulate the S2 and/or S3-5 nerve roots bilaterally.

Figure 39:
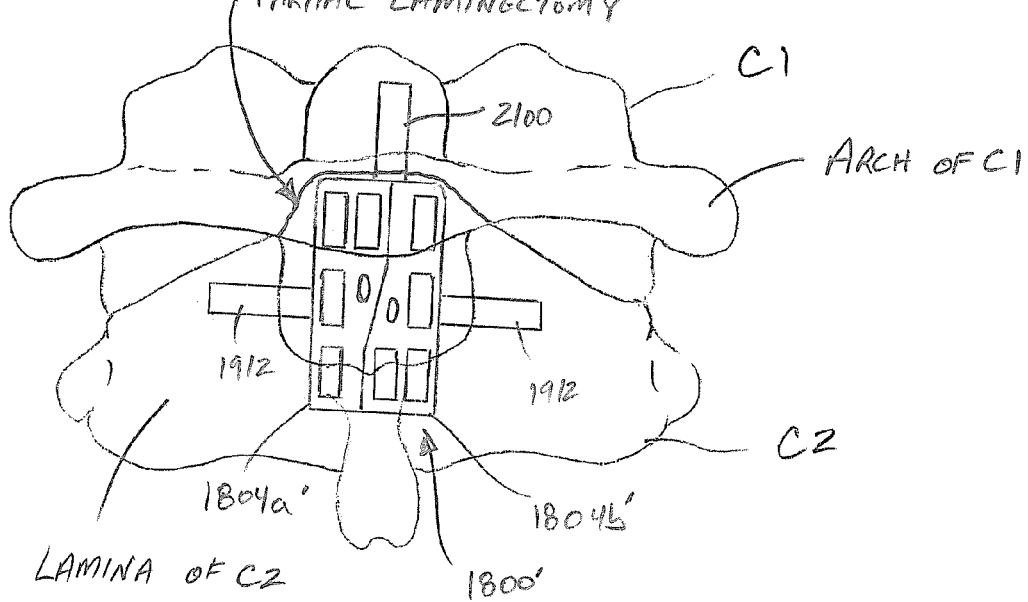
FIGS. 39-43 are side and posterior views of the C1-C2 cervical vertebrae with exemplary uses of embodiments of the present invention.

Referring now to FIGS. 39-43, and by way of example and not limitation, several illustrative examples of the placement of the electrode paddles of the present invention between the C1-C2 cervical vertebrae are shown. Referring now to FIG. 39, electrode paddle 1800' is shown with its paddle sections 1804a' and 1804b' still interconnected with the electrodes positioned to stimulate neural structures of the spinal canal. The electrode paddle 1800' shown in FIG. 39 has its longitudinal axis aligned substantially parallel to the axis of the spine. The flanges 1912 and 2100 are tucked under a portion of the lamina of the C1 and C2 cervical vertebrae to maintain the location of the electrode paddle 1800'.

Figure 1A:
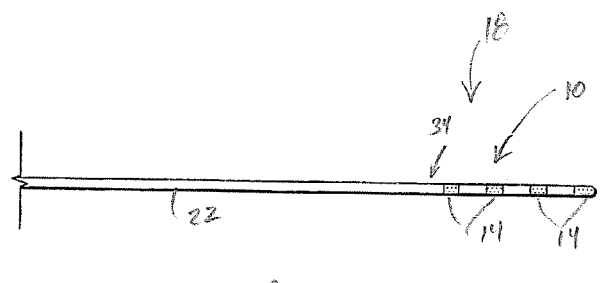
FIGS. 1A-1C are plan views of electrode arrays known in the prior art.
Figure 1B:
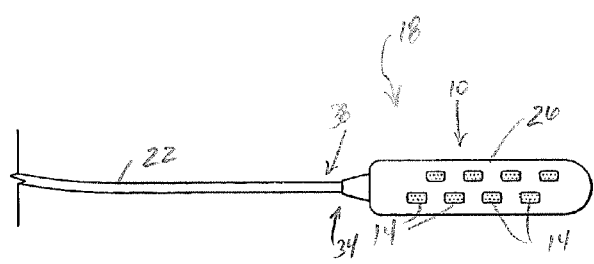
Figure 1C:
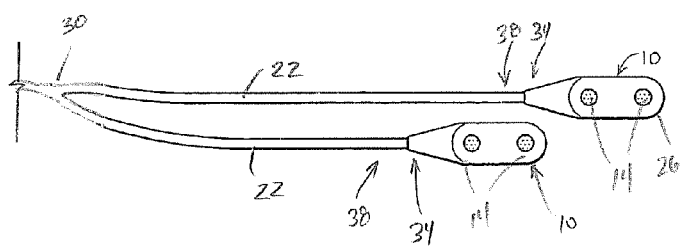
Figure 1E:
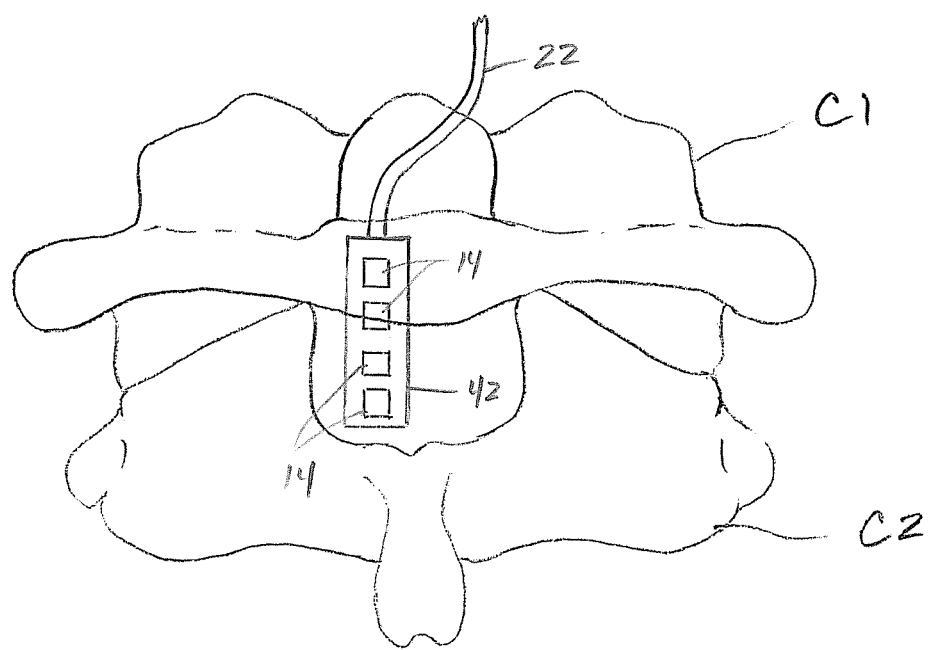
FIG. 1E is a rear view of an electrode paddle implanted proximate the C1 and C2 cervical vertebrae.
Figure 40:
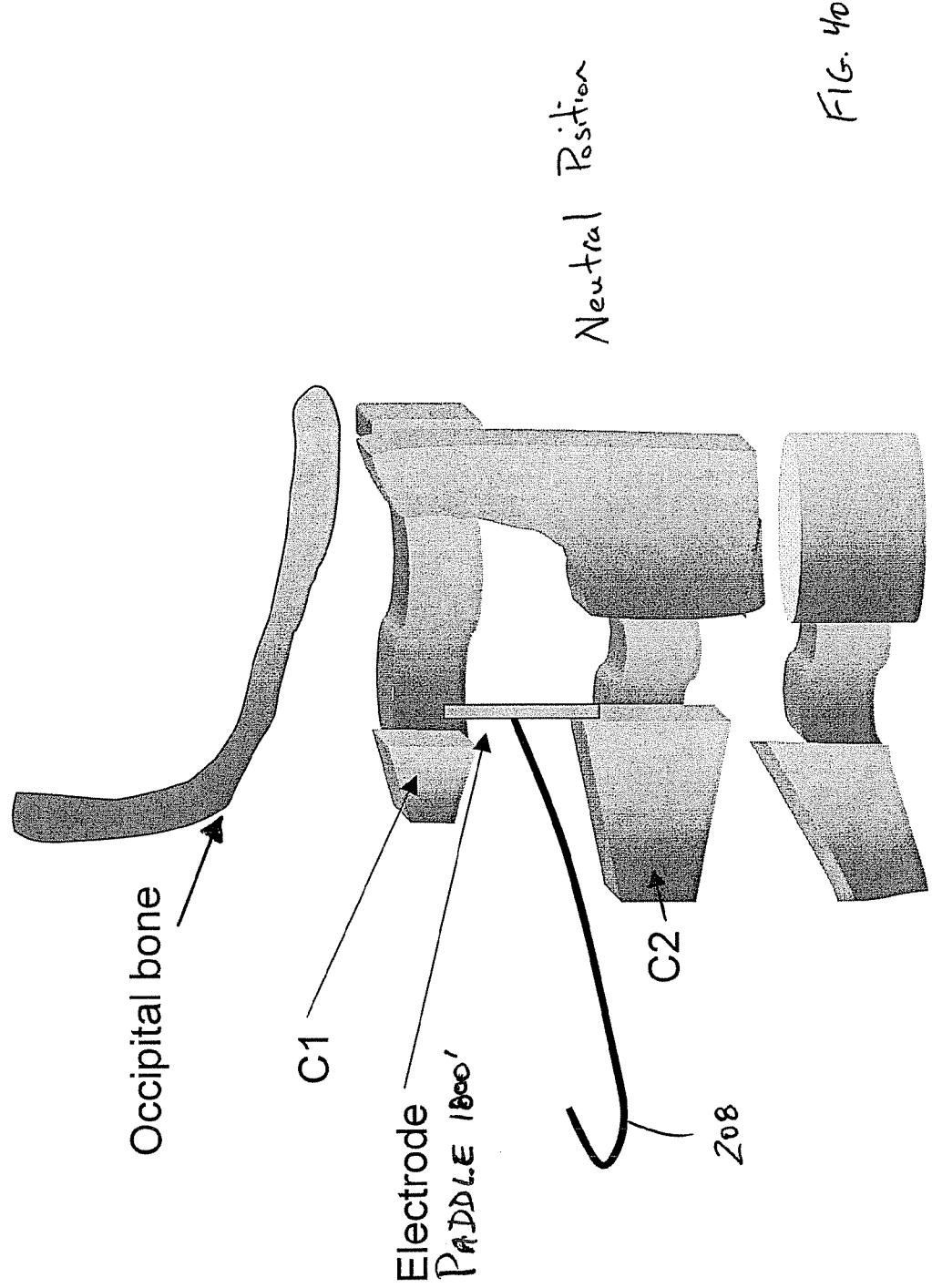
Figure 41:
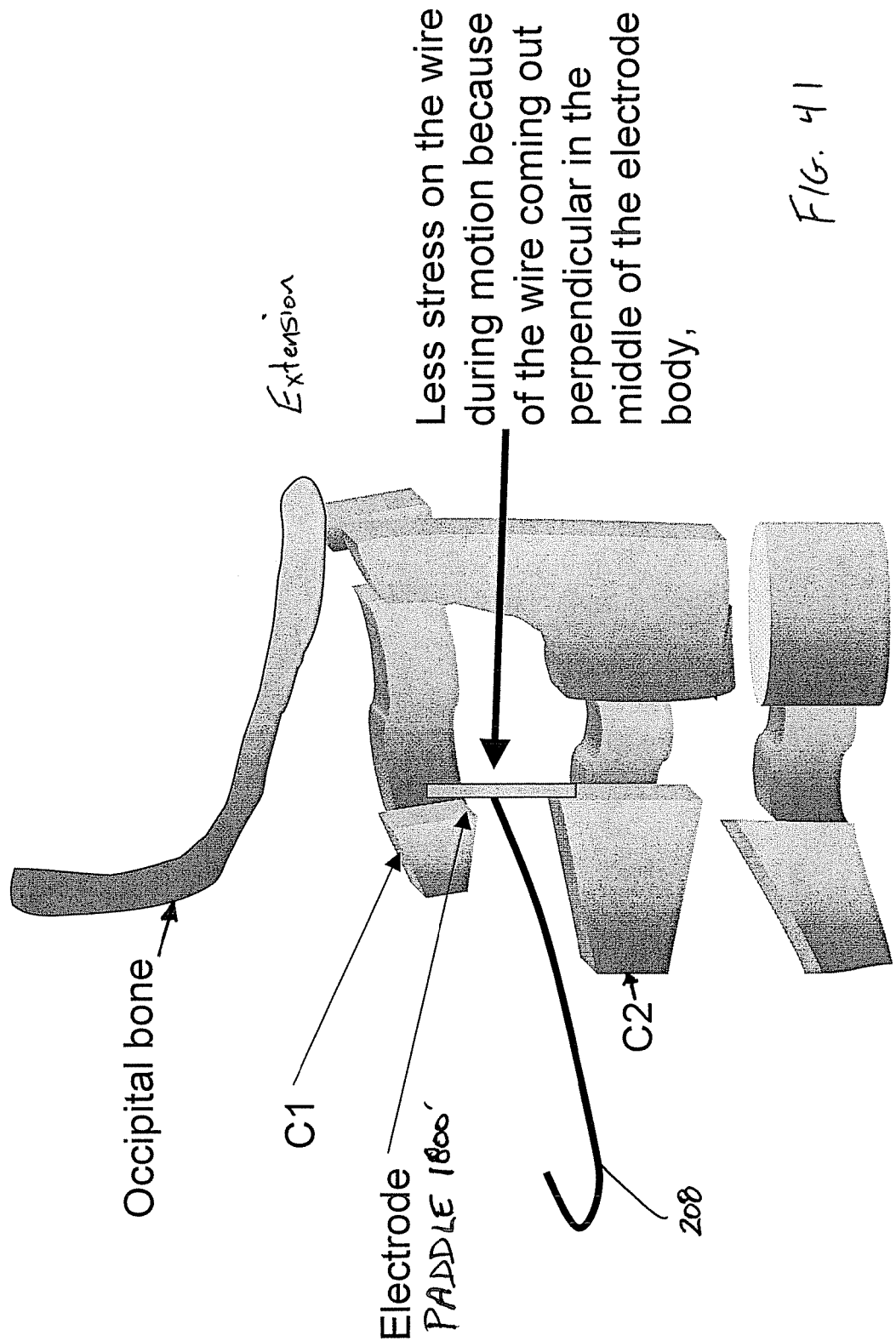

FIG. 40 illustrates a partial side view of the electrode paddle 1800' placed between the C1 and C2 vertebrae, wherein the vertebrae in a neutral position. FIG. 41 illustrates the electrode paddle 1800' of FIG. 40, but with vertebrae in extension. Here, the position of the lead 208 and its connection to the electrode paddle 1800' are preserved structurally because the lead 208 extends from the electrode paddle 1800' in a substantially perpendicular orientation. This reduces the stress on the electrode paddle 1800' and the lead 208, thereby helping preserve the integrity of the implanted stimulation components. This is in significant contrast stress conditions imposed on the electrode lead 22 and electrode paddle 42 described above and shown in FIG. 1F.

Figure 42:
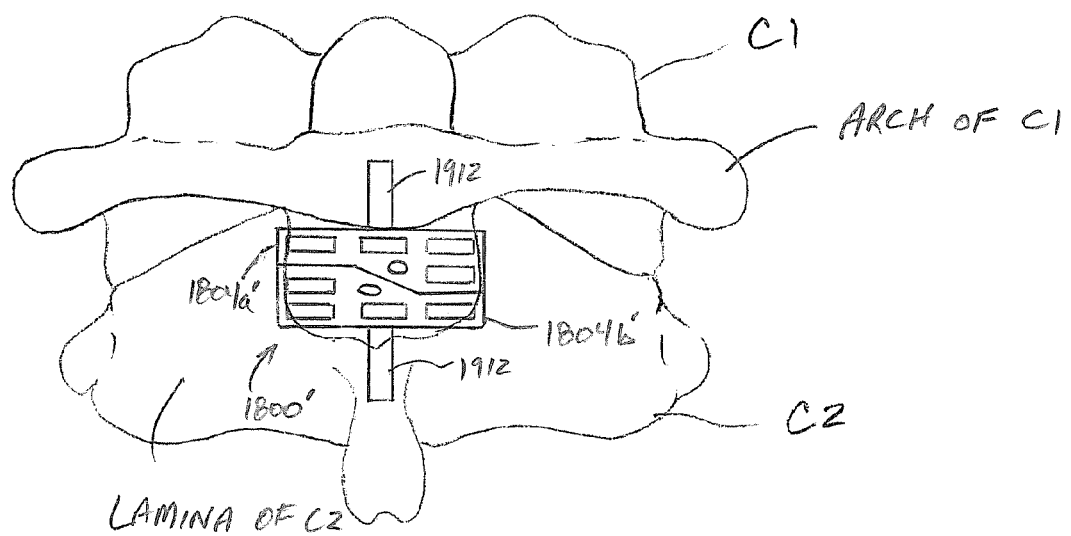

FIG. 42 illustrates another example of electrode paddle 1800' being used to with its paddle sections 1804a' and 1804b' still interconnected. The electrode paddle 1800' shown in FIG. 42 has its longitudinal axis aligned substantially perpendicular to the axis of the spine.

Figure 43:
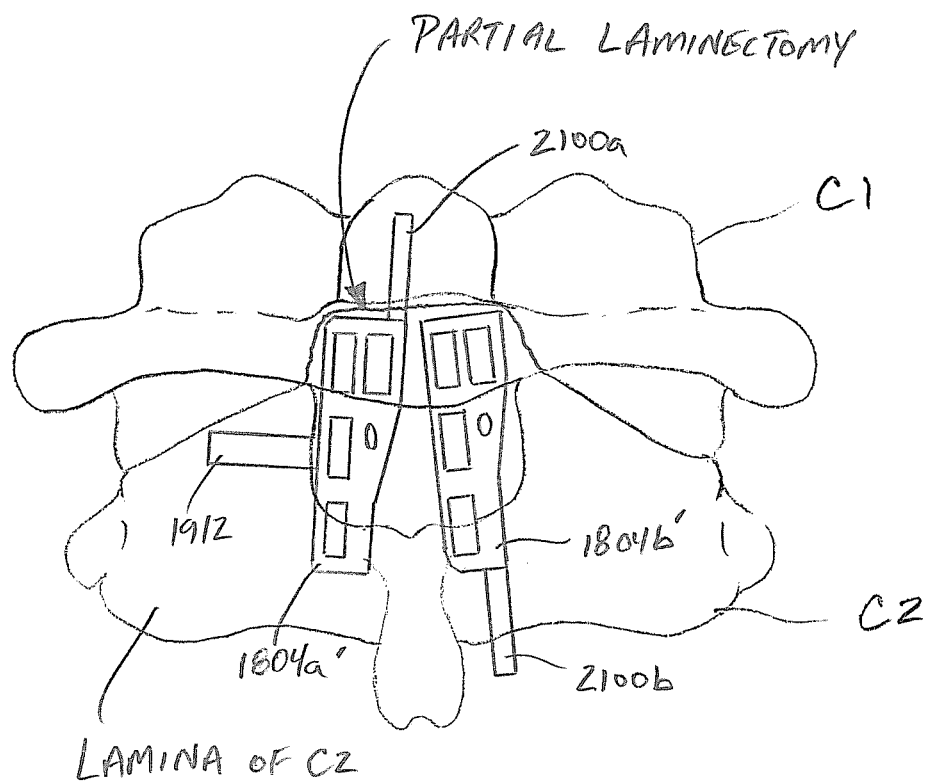

FIG. 43 illustrates the use of paddle sections 1804a' and 1804b' of electrode paddle 1800' where the paddle sections 1804a' and 1804b' have been separated from one another and are placed to stimulate the neural structures at C1-C2 bilaterally. As shown in FIG. 43, paddle section 1804b' has been separated from paddle section 1804a' by dividing bridging longitudinal flange 2100. The flanges 1912 and 2100 are tucked under a portion of the lamina of the C1 and C2 cervical vertebrae to maintain the location of the paddle sections 1804a' and 1804b'.

Referring now to FIGS. 44-46, and by way of example and not limitation, several illustrative examples of the placement of the electrode paddles of the present invention between the T7-T11 thoracic vertebrae are shown. Referring now to FIG. 44, electrode paddle 2200 is shown with its paddle sections 2204a and 2204b still interconnected with the electrodes positioned to stimulate neural structures of the spinal cord located between the T9 and T10 thoracic vertebrae. The dorsally projecting lead connections 2208a and 2208b allows the paddle sections 2204a and 2204b to cover the targeted neural structures with the leads 208 positioned to extend between the T9 and T10 vertebrae.

FIG. 45 illustrates the use of paddle sections 2204a and 2204 of electrode paddle 2200 where the paddle sections 2204 and 2204 have been separated from one another and are placed to stimulate the spinal cord between the T9 and T10 vertebrae in the case of paddle section 2204b, and the spinal cord between the T10 and T11 vertebrae in the case of paddle section 2204a. Thus, one electrode paddle can be used to stimulate neural structures at a plurality of levels of the spine.

Referring now to FIG. 46, the electrode paddle section 2204a of FIG. 45 has been rotated 180 degrees to provide an alternate orientation for stimulation of the neural structures relative to that shown in FIG. 45. Thus, the asymmetrical electrode configuration of the paddle sections of at least some embodiments of the present invention allow the electrode paddles to be divided into paddle sections for modified treatment orientations, as may be desired by the treating physician.

Embodiments of the present invention include an electrode paddle, such as electrode paddle 1800, wherein one of the paddle sections, such as paddle section 1804a or 1804b, is a blank; that is, it does not contain any contacts 220 (or if it does have contacts, the contacts are not interconnected to the implantable pulse generator, and/or they are not controlled by the implantable pulse generator). A blank paddle section may be used to augment securing the position of the paddle section having an active contact, or the blank paddle section may be separated from the paddle section having an active contact. Thus, for the electrode paddles described herein, the electrode paddle may have at least one detachably attached paddle section that has a contact.

Embodiments of the present invention include methods of using an implantable electrode paddle of the present invention. The method includes a surgeon making an incision for implanting an electrode paddle of the present invention. If the patient's physiological needs are such that the electrode paddle should be divided, the surgeon can separate the paddle sections to accommodate the needs of the patient and implant the paddle sections to stimulate the target neural structures. The surgeon may implant a new pulse generator with an electrode paddle of the present invention, or the surgeon may use a previously implanted pulse generator as the electrical source.

Embodiments of the present invention also include a method of assembling an implantable neuron-stimulation system. The method includes the step of providing an electrode paddle having a plurality of separable paddle sections, wherein in at least one paddle section the contacts are configured asymmetrically.

Embodiments of the present invention further include a method of assembling an implantable system, the method comprising: providing a pulse generator and an electrical lead, and further comprising the step of preparing an electrode paddle by dividing the electrode paddle into a plurality of paddle sections.

Electrode paddles and their associated features may be made from one or more materials that possess the appropriate strength characteristics necessary to withstand conditions from the body and associated implants when used in medical applications. In addition, the materials may be chosen to provide desired flexibility characteristics. In accordance with embodiments of the present invention, examples of materials that may be used include, but are not necessarily limited to, silicone, polyether ether plastics, such as ketone (PEEK), polyether ketone ketone (PEKK), ultra high molecular weight polyethylene (UHMWPE), and polymethylmethacrylate (PMMA); metals, such as titanium and stainless steel; composites; as well as other tissue compatible materials. The material used will depend upon the portion of the device under consideration, and certain materials may be more appropriate than others.

While particular embodiments of the present invention have been described in some detail, it should be understood that other related embodiments are intended to be within the scope of the present invention. For example, other ways to functionally and structurally provide a flange or a dorsally projecting electrode lead are encompassed by the present invention, whether such structures employ all or only some aspects of the present invention, and/or whether such structures are integrally made or form a connectable part of the an implantation system, and/or whether such structures include other features that are well within the knowledge of those of ordinary skill in this art, and/or whether such structures are conventional structures or those that may be developed in the future.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

While various embodiments of the present invention have been described in detail, it is apparent that modifications and adaptations of those embodiments will occur to those skilled in the art. However, it is to be expressly understood that such modifications and adaptations are within the spirit and scope of the present invention, as set forth in the following claims.

What is claimed:

1. An electrode paddle for use in an implantable neurostimulation system for implanting into a patient to stimulate neural structures within the patient, the implantable neurostimulation system including an implantable pulse generator and an electrode lead, the electrode lead in electrical communication with the implantable pulse generator, the implantable pulse generator for sending an electrical current to the electrode paddle by way of the electrode lead, the electrode paddle comprising:
    a plurality of paddle sections formed of an implantable tissue compatible material including a first paddle section and a second paddle section wherein each of the plurality of paddle sections includes a stimulation surface including a plurality of conductive contacts in electrical communication with the electrode lead and an opposing insulating surface, the first paddle section detachably attached to the second paddle section;
    a stabilization flange formed of an implantable tissue compatible material located along at least a portion of at least one exterior side edge of a plurality of side edges of the first paddle section, wherein the at least one exterior side edge of the plurality of side edges of the first paddle section faces away from each of the plurality of paddle sections;
    a lead connection joined to the opposing insulating surface of the first paddle section and extending substantially perpendicular away from the opposing insulating surface of the first paddle section, the lead connection spaced from the first end, second end, first lateral side, and second lateral side;
    a plurality of electrical conductors extending through the lead connection to the plurality of conductive contacts disposed on the stimulation surface of the first paddle section; and wherein the stimulation surface lies within a first plane, and the stabilization flange lies within a second plane, the second plane intersecting the first plane.

2. The electrode paddle of claim 1, wherein the flange is angled and non-planar relative to the dorsal surface of the first paddle section.

3. The electrode paddle of claim 1, wherein the flange comprises a gap, the gap extending from an outer lateral edge of the flange to the at least one exterior side edge of the first paddle section.

4. The electrode paddle of claim 1, wherein at least two contacts of each of the first and second paddle sections are aligned along a first axis and at least two contacts of each of the first and second paddle sections are aligned along a second axis, and wherein the first axis and the second axis are substantially perpendicular to one another.

5. The electrode paddle of claim 1, wherein at least one contact of the plurality of contacts of the first paddle section is offset laterally from a linearly aligned group of the plurality of contacts.

6. The electrode paddle of claim 1, wherein the stimulation surface defines a plane and the lead connection intersects the plane containing the stimulation surface.

7. The electrode paddle of claim 1, wherein the electrical conductors include a coupling end spaced from the first paddle section and further including a pulse generator having a passage to receive the coupling end, wherein the pulse generator is configured to selectively energize the electrical conductors to thereby energize the interconnected conductive electrodes.

8. The electrode paddle of claim 1, wherein the stabilization flange extends laterally away from the first lateral side of the first paddle section, the stabilization flange configured to engage adjacent tissue of a patient to stabilize the position of the electrode paddle.

9. The electrode paddle of claim 8, wherein the stabilization flange further includes at least one groove extending laterally away from the lateral side.

10. An implantable neurostimulation apparatus, comprising:
    a paddle lead section formed of an insulating tissue compatible material having a stimulation side surface including a plurality of conductive electrodes disposed thereon and an opposing insulating surface, wherein the paddle has a thickness between the stimulation side surface and the opposing insulating surface, the paddle lead section further including a length extending along a longitudinal axis between a first end and an opposing second end, and a width extending between a first lateral side and an opposing second lateral side, the length being greater than the width and the width being greater than the thickness;
    a lead connection portion joined to the insulating side and extending away from the insulating side, the lead connection spaced from the first end, second end, first lateral side and second lateral side, the lead connection portion extending away from the insulating side in a direction substantially perpendicular to the longitudinal axis of the paddle lead section; and
    a plurality of electrical conductors extending through the lead connection to the plurality of conductive electrodes disposed on the stimulation side surface of the paddle lead section; and further including a stabilization flange formed of tissue compatible material and extending laterally away from the first lateral side, wherein the stabilization flange is configured to engage adjacent tissue of a patient to stabilize the position of the paddle lead section, wherein the stimulation surface lies within a first plane, and the stabilization flange lies within a second plane, the second plane intersecting the first plane.

11. The apparatus of claim 10, wherein the stimulation side surface defines a plane and the lead connection portion intersects the plane containing the stimulation side surface.

12. The apparatus of claim 10, wherein the stabilization flange further includes at least one groove extending laterally away from the lateral side.

13. The apparatus of claim 10, further including a second paddle lead section formed of an insulating tissue compatible material having a stimulation side surface including a plurality of conductive electrodes disposed thereon and an opposing insulating surface, wherein the paddle has a thickness between the stimulation side surface and the opposing insulating surface, the paddle lead section further including a length extending along a longitudinal axis between a first end and an opposing second end, and a width extending between a first lateral side and an opposing second lateral side, the length being greater than the width and the width being greater than the thickness;
- a second lead connection portion joined to the insulating side and extending away from the insulating side, the lead connection spaced from the first end, second end, first lateral side and second lateral side; and
- a plurality of electrical conductors extending through the lead connection to the plurality of conductive electrodes disposed on the stimulation side surface of the paddle lead section; wherein the second paddle lead section is detachably joined to the paddle lead section.

14. The apparatus of claim 10, wherein the plurality of conductive electrodes are disposed asymmetrically on the stimulation side surface.

\* \* \* \* \*